US011992351B2

(12) United States Patent
Jones et al.

(10) Patent No.: US 11,992,351 B2
(45) Date of Patent: May 28, 2024

(54) METHOD, APPARATUS, AND SYSTEM FOR ENERGY-RESOLVED SCATTER IMAGING DURING RADIATION THERAPY

(71) Applicant: Rush University Medical Center, Chicago, IL (US)

(72) Inventors: Kevin Chapman Jones, Chicago, IL (US); Julius V. Turian, Chicago, IL (US); James C. h. Chu, Oak Brook, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 16/630,350

(22) PCT Filed: Jul. 12, 2018

(86) PCT No.: PCT/US2018/041824
§ 371 (c)(1),
(2) Date: Jan. 10, 2020

(87) PCT Pub. No.: WO2019/014447
PCT Pub. Date: Jan. 17, 2019

(65) Prior Publication Data
US 2020/0155098 A1    May 21, 2020

Related U.S. Application Data

(60) Provisional application No. 62/532,211, filed on Jul. 13, 2017.

(51) Int. Cl.
*A61B 6/00*    (2006.01)
*A61B 6/12*    (2006.01)
(Continued)

(52) U.S. Cl.
CPC ........... *A61B 6/483* (2013.01); *A61B 6/12* (2013.01); *A61B 6/4241* (2013.01); *A61B 6/481* (2013.01);
(Continued)

(58) Field of Classification Search
None
See application file for complete search history.

(56) References Cited

U.S. PATENT DOCUMENTS 4,870,667 A * 9/1989 Brunnett ............... G01T 1/202
378/19
5,532,944 A * 7/1996 Battista ................. G01T 1/17
708/3
(Continued)

FOREIGN PATENT DOCUMENTS

| JP | 200782663 A | 4/2007 |
| JP | 2008302211 A | 10/2008 |
| WO | 2016172312 A1 | 10/2016 |

OTHER PUBLICATIONS

Nguyen et al., "Apparent Image Formation by Compton-Scattered Photons in Gamma-Ray Imaging," IEEE Signal Processing Letters, vol. 8, No. 9, (2001), pp. 248-251.
(Continued)

*Primary Examiner* — Edwin C Gunberg
(74) *Attorney, Agent, or Firm* — Barnes & Thornburg LLP

(57) ABSTRACT

The disclosure is directed to an apparatus, system, and method for performing energy-resolved scatter imaging during radiation therapy upon a patient. The apparatus includes a radiation detector capable of resolving the energy of the scattered photons due to Compton scattering during radiation therapy. The radiation detector outputs a first signal when photon energy of the detected photons is within a first energy range and a second signal when photon energy of the
(Continued)

detected photons is within a second energy range. The apparatus also includes an image controller configured to receive the first and second signal and obtain an energy-resolved scatter image data set. The energy-resolved scatter imaging improves the contrast and sensitivity for identification of different tissue types. Therefore, tumor tracking during radiation therapy and image guidance during radiotherapy are improved.

18 Claims, 22 Drawing Sheets

(51) Int. Cl.
  A61B 6/42       (2024.01)
  A61N 5/10       (2006.01)
(52) U.S. Cl.
  CPC ............ *A61B 6/482* (2013.01); *A61B 6/5205* (2013.01); *A61N 5/10* (2013.01)

(56) References Cited

U.S. PATENT DOCUMENTS

| | | | | |
|---|---|---|---|---|
| 5,821,541 | A * | 10/1998 | Tumer | A61B 6/037 250/370.09 |
| 6,087,665 | A * | 7/2000 | Hoffman | G01T 1/2008 250/483.1 |
| 10,371,830 | B2 * | 8/2019 | Jacobs | G01T 1/1642 |
| 10,674,973 | B2 * | 6/2020 | Chu | A61B 6/483 |
| 2004/0021083 | A1 * | 2/2004 | Nelson | G01T 1/1644 250/370.09 |
| 2006/0081899 | A1 * | 4/2006 | Fritzler | G01T 1/242 257/291 |
| 2007/0158573 | A1 * | 7/2007 | Deych | G01T 1/2985 250/370.11 |
| 2008/0011960 | A1 * | 1/2008 | Yorkston | G21K 4/00 250/370.09 |
| 2009/0296887 | A1 * | 12/2009 | Boyden | G01T 1/161 378/87 |
| 2010/0034348 | A1 * | 2/2010 | Yu | A61B 6/4233 378/209 |
| 2010/0104505 | A1 | 4/2010 | Michael | |
| 2016/0206256 | A1 | 7/2016 | Berglund et al. | |
| 2016/0256713 | A1 * | 9/2016 | Saunders | A61N 5/1049 |
| 2018/0140265 | A1 * | 5/2018 | Chu | A61B 6/483 |

OTHER PUBLICATIONS

Nguyen et al., "On a Novel Approach to Compton Scattered Emission Imaging," IEEE Transactions on Nuclear Science, vol. 56, No. 3, (2009), pp. 1430-1437.
International Search Report, issued in PCT/US2018/041824, dated Oct. 1, 2018.
International Preliminary Report on Patentability, issued in PCT/US2018/041824, dated Jan. 14, 2020.
P. G. Lale, "The Examination of Internal Tissues, using Gamma-ray Scatter with a Possible Extension to Megavoltage Radiography," Physics in Medicine and Biology 4, 159 (1959).
F. T. Farmer and M. P. Collins, "A new approach to the determination of anatomical cross-sections of the body by Compton scattering of gamma-rays," Phys Med Biol 16, 577-586 (1971).
R. L. Clarke, E. N. Milne and G. Van Dyk, "The use of Compton scattered gamma rays for tomography," Investigative radiology 11, 225-235 (1976).
G. Harding and R. Tischler, "Dual-energy Compton scatter tomography," Physics in Medicine and Biology 31, 477 (1986).
S. J. Norton, "Compton scattering tomography," Journal of Applied Physics 76, 2007-2015 (1994).

M. Lenti, "A 3-D imaging device using Compton scattering off the body," Nuclear Instruments and Methods in Physics Research Section A: Accelerators, Spectrometers, Detectors and Associated Equipment 588, 457-462 (2008).
D. W. Mundy and M. G. Herman, "Uncertainty analysis of a Compton camera imaging system for radiation therapy dose reconstruction," Medical physics 37, 2341-2350 (2010).
K. P. MacCabe, A. D. Holmgren, M. P. Tornai and D. J. Brady, "Snapshot 2D tomography via coded aperture x-ray scatter imaging," Appl. Opt. 52, 4582-4589 (2013).
E. Odeblad and Å. Norhagen, "Measurements of Electron Densities with the Aid of the Compton Scattering Process," Acta Radiologica os-45, 161-167 (1956).
R. L. Clarke and G. Van Dyk, "A new method for measurement of bone mineral content using both transmitted and scattered beams of gamma-rays," Phys Med Biol 18, 532-539 (1973).
J. J. Battista, L. W. Santon and M. J. Bronskill, "Compton scatter imaging of transverse sections: corrections for multiple scatter and attenuation," Phys Med Biol 22, 229-244 (1977).
J. J. Battista and M. J. Bronskill, "Compton scatter imaging of transverse sections: an overall appraisal and evaluation for radiotherapy planning," Phys Med Biol 26, 81-99 (1981).
H. Yan, Z. Tian, Y. Shao, S. B. Jiang and X. Jia, "A new scheme for real-time high-contrast imaging in lung cancer radiotherapy: a proof-of-concept study," Phys Med Biol 61, 2372-2388 (2016).
G. Redler, D. Bernard, A. Templeton, C. Kumaran Nair, J. Turian and J. Chu, "MO-AB-BRA-2: A Novel Scatter Imaging Modality for Real-Time Image Guidance During Lung SBRT," in AAPM 57th Annual Meeting and Exhibition, (Anaheim, CA, 2015).
H. Zaidi and K. F. Koral, "Scatter modelling and compensation in emission tomography," European journal of nuclear medicine and molecular imaging 31, 761-782 (2004).
B. F. Hutton, I. Buvat and F. J. Beekman, "Review and current status of SPECT scatter correction," Phys Med Biol 56, R85-112 (2011).
R. L. Siddon, "Fast calculation of the exact radiological path for a three-dimensional CT array," Medical physics 12, 252-255 (1985).
R. L. Clarke and G. Van Dyk, "Compton-Scattered Gamma Rays in Diagnostic Radiography," Medical Radioisotope Scintigraphy. vol. I. Vienna, International Atomic Energy Agency 1, 247-680 (1969).
F. T. Farmer and M. P. Collins, "A further appraisal of the Compton scattering method for determining anatomical cross-sections of the body," Phys Med Biol 19, 808-818 (1974).
J. J. Battista and M. J. Bronskill, "Compton-scatter tissue densitometry: calculation of single and multiple scatter photon fluences," Phys Med Biol 23, 1-23 (1978).
A. L. Boyer and E. C. Mok, "Calculation of photon dose distributions in an inhomogeneous medium using convolutions," Medical physics 13, 503-509 (1986).
E. Wong, Y. Zhu and J. Van Dyk, "Theoretical developments on fast Fourier transform convolution dose calculations in inhomogeneous media," Medical physics 23, 1511-1521 (1996).
T. Goorley, M. James, T. Booth, F. Brown, J. Bull, L. J. Cox, J. Durkee, J. Elson, M. Fensin, R. A. Forster, J. Hendricks, H. G. Hughes, R. Johns, B. Kiedrowski, R. Martz, S. Mashnik, G. McKinney, D. Pelowitz, R. Prael, J. Sweezy, L. Waters, T. Wilcox and T. Zukaitis, "Initial MCNP6 Release Overview," Nuclear Technology 180, 298-315 (2012).
R. McConn Jr., C. Gesh, R. Pagh, R. Rucker and R. Williams III, "Compendium of Material Composition Data for Radiation Transport Modeling," PNNL-15870 Rev. 1 (2011).
J. H. Hubbell and S. M. Seltzer, "Tables of X-Ray Mass Attenuation Coefficients and Mass Energy-Absorption Coefficients from 1 keV to 20 MeV for Elements Z=1 to 92 and 48 Additional Substances of Dosimetric Interest," in NISTIR 5632, (1996).
G. Harding, "Inelastic photon scattering: Effects and applications in biomedical science and industry," Radiation Physics and Chemistry 50, 91-111 (1997).
P. G. Lale, "The Examination of Internal Tissues by High-Energy Scattered X Radiation," Radiology 90, 510-517 (1968).

* cited by examiner

1st-Order Scattered Photon

4th-Order Scattered Photon

METHOD, APPARATUS, AND SYSTEM FOR ENERGY-RESOLVED SCATTER IMAGING DURING RADIATION THERAPY

U.S. PROVISIONAL BENEFIT

This application is a National Stage application of International Application No. PCT/US2018/041824, filed Jul. 12, 2018, which claims the benefit of U.S. Provisional Application No. 62/532,211, filed Jul. 13, 2017.

BACKGROUND

1. Technical Field

In radiation therapy upon a tumor in a patient, the tumor is irradiated by an external beam with megavoltage X-ray radiation (photons). During this process, a fraction of the therapeutic radiation (photons) are scattered into all directions surrounding the point of interaction between the therapeutic photon and tissue. By detecting the scattered photons and resolving the energy of the detected scattered photons, energy-resolved scatter imaging may be performed, providing a high-contrast imaging to track tumor position during radiation therapy.

2. Background Information

In external beam radiation therapy, the tumor is irradiated with megavoltage X-ray photons. An important photon interaction for megavoltage X-ray is Compton-scattering, which dominates for low atomic number (Z<8) materials over approximately the energy range between 0.026 MeV and 24 MeV. During Compton-scattering, an incident photon scatters into a different direction with a longer wavelength with lower energy. Since Compton-scattered radiation (photons) carry information about the irradiated volume, the scattered radiation is used to form a scatter image for imaging the irradiated volume. However, the image contrast of previous scatter imaging methods is not good enough for some applications, and some extra information (for example, energy information of the scattered photons) is lost in previous scatter imaging methods. Energy-resolved scatter imaging as described below improves the image contrast and obtain more information of the scattered photons compared to previous scatter imaging methods.

BRIEF SUMMARY

The present disclosure is directed to a method for performing energy-resolved scatter imaging during radiation therapy upon a patient. The method includes detecting, by a device comprising a radiation detector, a collimator in front of the radiation detector, and an image controller in communication with the radiation detector, a first signal and a second signal from a portion of scattered radiation from a treatment region in a patient delivered from a radiation source to the treatment region in the patient, the first signal having a first photon energy in a first energy range and the second signal having a second photon energy in a second energy range, the second energy range being different than the first energy range. The method also includes converting, by the device, the first signal into a first image data set and the second signal into a second image data set, and processing, by the device, an image operation on the first and second image data sets to obtain an energy-resolved scatter image data. Furthermore, the method includes distinguishing, by the device, normal tissue from diseased tissue in the treatment region using the energy-resolved scatter image data.

The present disclosure describes an apparatus for performing energy-resolved scatter imaging during radiation therapy upon a patient. The apparatus includes a collimator comprising an opening, the collimator configured to allow a portion of scattered radiation from a treatment region in a patient to pass through the opening. The apparatus also includes a radiation detector configured to detect the portion of scattered radiation passing through the opening, the radiation detector providing a first signal when photon energy of the detected portion of scattered radiation is within a first energy range and the radiation detector providing a second signal when photon energy of the scattered radiation is within a second energy range, wherein the first energy range is different from the second energy range. Furthermore, the apparatus includes an image controller configured to receive the first signal and the second signal from the radiation detector, wherein the image controller is configured to convert the first signal into a first image data set and the second signal into a second image data set, and perform an image operation on the first and second image data sets to obtain an energy-resolved scatter image data set.

The present disclosure also describes a system for performing energy-resolved scatter imaging during radiation therapy upon a patient. The system includes a radiation source configured to deliver a radiation beam to a treatment region and a collimator comprising an opening, the collimator configured to allow a portion of scattered radiation from a treatment region in a patient to pass through the opening. The system also includes a radiation detector configured to detect the portion of scattered radiation passing through the opening, the radiation detector providing a first signal when photon energy of the detected portion of scattered radiation is within a first energy range and the radiation detector providing a second signal when photon energy of the scattered radiation is within a second energy range, wherein the first energy range is different from the second energy range. The system further includes an image controller configured to receive the first signal and the second signal from the radiation detector, and the image controller is configured to convert the first signal into a first image data set and the second signal into a second image data set, and perform an image operation on the first and second image data sets to obtain an energy-resolved scatter image data set.

DETAILED DESCRIPTION OF THE DRAWINGS

The invention will now be described in detail hereinafter with reference to the accompanied drawings, which form a part of the present invention, and which show, by way of illustration, specific examples of embodiments. Please note that the invention may, however, be embodied in a variety of different forms and, therefore, the covered or claimed subject matter is intended to be construed as not being limited to any of the embodiments to be set forth below. Please also note that the invention may be embodied as methods, devices, components, or systems. Accordingly, embodiments of the invention may, for example, take the form of hardware, software, firmware or any combination thereof.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter includes combinations of exemplary embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" or "at least one" as used herein, depending at least in part upon context, may be used to describe any feature, structure, or characteristic in a singular sense or may be used to describe combinations of features, structures or characteristics in a plural sense. Similarly, terms, such as "a", "an", or "the", again, may be understood to convey a singular usage or to convey a plural usage, depending at least in part upon context. In addition, the term "based on" or "determined by" may be understood as not necessarily intended to convey an exclusive set of factors and may, instead, allow for existence of additional factors not necessarily expressly described, again, depending at least in part on context.

Figure 1:
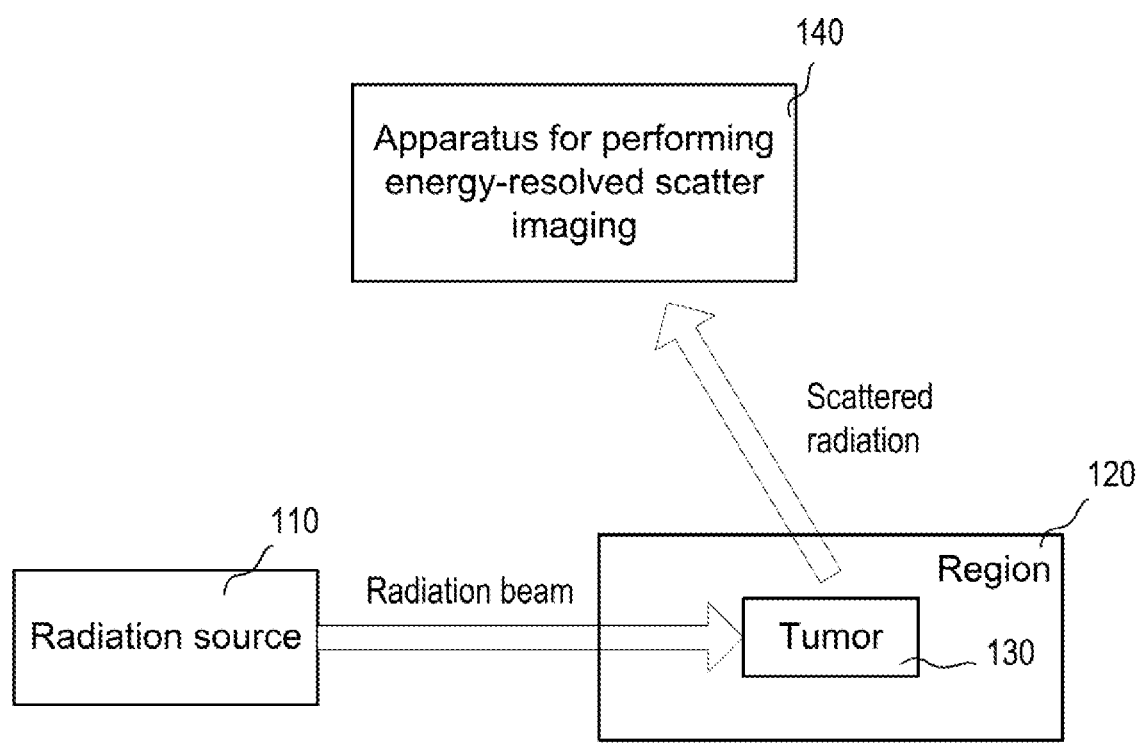
FIG. 1 is a schematic diagram of a system for performing energy-resolved scatter imaging during radiation therapy upon a patient.

FIG. 1 shows a schematic diagram of a system for performing energy-resolved scatter imaging during radiation therapy of a patient. The system can include a radiation source 110, the patient having a region 120 with or having a tumor 130, and an apparatus for performing energy-resolved scatter imaging 140.

The radiation source 120 generates high energy radiation and is positioned to deliver the high energy radiation to the tumor 130 in the region 120 of the patient as a radiation beam. For example, the radiation source 120 may be a linear accelerator, which generates radiation by bombarding a target with electrons. In other embodiments, other sources of radiation suitable for the treatment of tumors may be used.

The tumor 130 in the region 120 is treated by the radiation therapy. For example, the tumor 130 may be a lung tumor. In other embodiments, the tumor may be other types of tumors suitable for undergoing radiation therapy. The patient having the tumor 130 is positioned on a patient positioning structure, which provides support for the patient during radiation therapy.

When the radiation beam is delivered to the region 120 with or having the tumor 130, the radiation, i.e, photons, of the radiation beam interacts with the tumor 130 in the region 120 and scatters in the region 120. One important photon interaction for megavoltage therapy radiation beams is Compton-scattering, which dominates for low atomic number (Z<8) materials over approximately the energy range between 0.026 MeV and 24 MeV, wherein 1 MeV equals to $10^6$ eV. During Compton-scattering, an incident photon scatters into a different direction with a longer wavelength with lower energy, and the lost energy is contributed to the kinetic energy of an electron. The other scattering process, for example, coherent scattering, is negligible over the considered energy range, and any further mention of scattering is in reference to Compton-scattering. By collecting these scattered photons with a detector, a scatter image may be formed.

The apparatus 140 for performing energy-resolved scatter imaging is capable of detecting the scattered radiation and forming energy-resolved scatter image data set. To create a scatter image with meaningful spatial resolution, the scattered photons may be restricted by origin of the scattered photons, for example, through collimation. Another way to determine the origin of the scattered photons is using multiple stage path tracking, for example, by using a gamma camera.

Figure 2A:
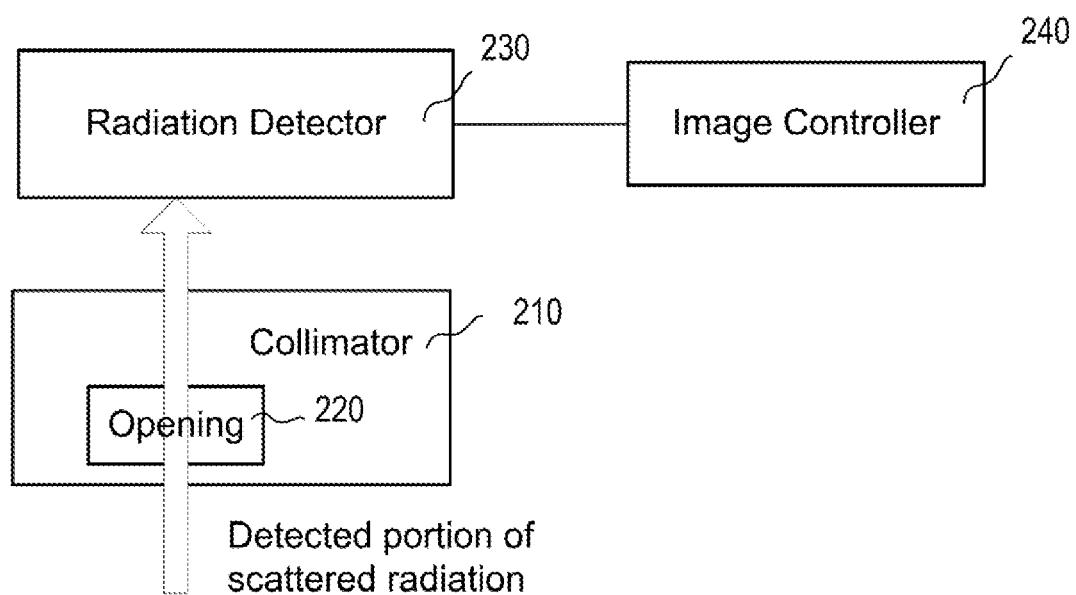
FIG. 2A is a schematic diagram of an apparatus for performing energy-resolved scatter imaging during radiation therapy.

As shown in FIG. 2A, one embodiment of the apparatus for performing energy-resolved scatter imaging may include a collimator 210 in front of a radiation detector 230 and an image controller 240.

The collimator 210 has an opening 220. The opening 220 of the collimator 210 only allows a small portion of the total scattered radiation passing through and reaching the radiation detector 230, therefore providing a way to spatially restrict the origin of the scattered photons. The type of the collimator may include but is not limited to a pinhole collimator, a multi-pinhole collimator, a coded aperture collimator, a jaw-based collimator, and a multi-leaf collimator. For one exemplary embodiment, the collimator 210 is a pinhole collimator, and the opening 220 is a pinhole. By way of non-limiting example, the diameter of the opening 220 (pinhole) may be adjustable from about 0.1 cm to 1 cm.

The size of the opening 220 may correlate with the spatial resolution of the scatter imaging. A larger opening may lead to larger, i.e., poor spatial resolution, with the benefit of more scattered photons passing through the opening to reach the radiation detector. A smaller opening may lead to smaller, i.e., better spatial resolution, with the drawbacks of fewer scattered photons passing through the opening to reach the radiation detector. Thus, the size of the opening 220 may be adjusted based on a plurality of variables, such as the specific requirement of the application, the sensitivity of the radiation detector, and the intensity of the scattered photons.

The radiation detector 230 is capable of detecting the scattered photons passing through the opening 220 of the collimator 210. The radiation detector 230 may include a plurality of radiation sensors positioned in an array, and output an electric signal when the scattered photons passing through the opening 220 reach the radiation detector. Each radiation sensor is capable of absorbing radiation photon reaching the radiation sensor and outputting an electric signal corresponding to the radiation photon. The electrical signal may comprise information corresponding to two-dimensional image data set.

In one embodiment, the radiation detector 230 may be capable of resolving the energy of the detected photon. For example, the radiation detector is able to determine whether the energy of the detected photon is within a first energy range. When the energy of the detected photon is determined to be within the first energy range, the radiation detector may output a first signal corresponding to the detected photons in the first energy range. Furthermore, the radiation detector is able to determine whether the energy of the detected photon is within a second energy range. When the energy of the detected photon is determined to be within the second energy range, the radiation detector may output a second signal corresponding to the detected photons in the second energy range. In other embodiment, the radiation detector 230 may be able to resolve the energy of the detected photon within more than two energy ranges, for example, there may be three, ten, or a hundred energy ranges and any interval in between.

In one embodiment, the radiation detector 230 may be formed from scintillator material, for example, CsI, coupled to amorphous silicon X-ray detectors and their associated electronics, and the opening of the collimator is formed from heavy, highly absorbing materials, for example, Tungsten or lead, with a conical cavity. When one photon is detected by the radiation detector, a detection event, i.e., an electric signal, is observed. The electric signal may have a shape like a spike, and the amplitude of the detection spike is proportional to the energy of the detected photon. Therefore, the photon energy of the detected photon may be determined by measuring the amplitude of the detection spike corresponding to the detected photon.

Figure 2B:
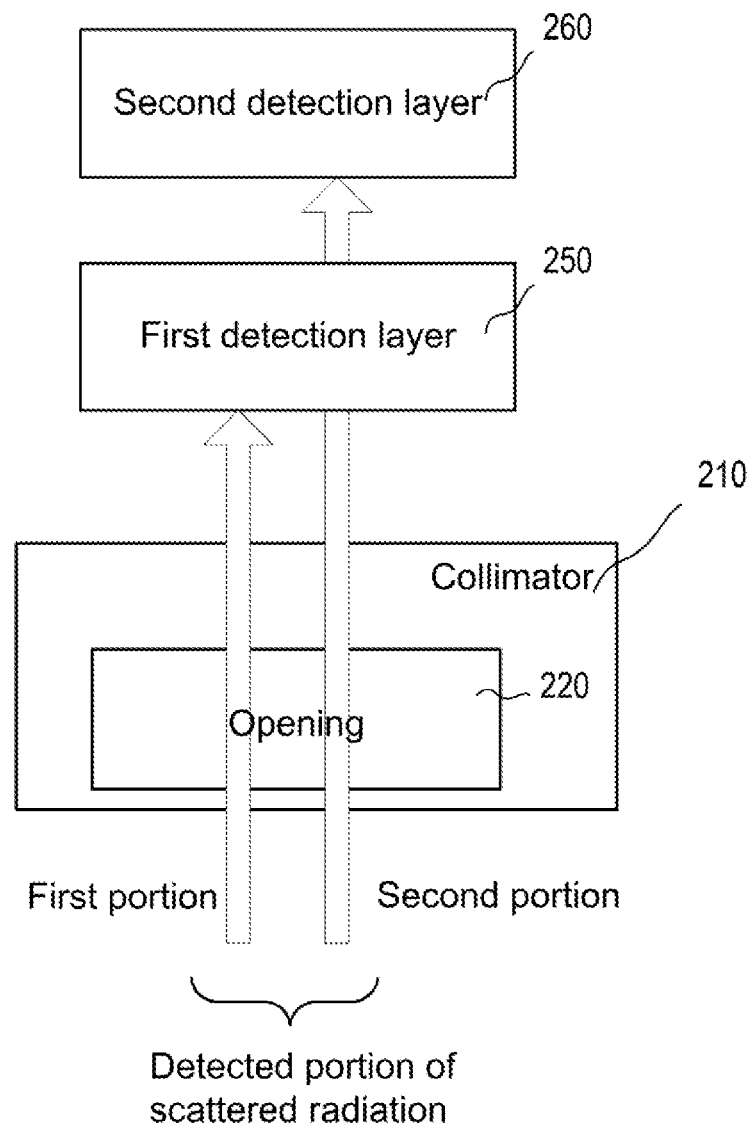
FIG. 2B illustrates one embodiment of the radiation detector for performing energy-resolved scatter imaging during radiation therapy.

In another embodiment, as shown in FIG. 2B, the radiation detector 230 may include a first detection layer 250 and a second detection layer 260. When photons pass through materials, such as a detection layer, lower energy photons are preferentially absorbed. Therefore, when the scattered photons passing through the opening 220 of the collimator 210 reach the first detection layer 250, a first portion of scattered photons corresponding to lower energy photons may be preferentially absorbed and detected by the first detection layer 250, so that the first detection layer 250 outputs a first signal corresponding to the first portion of scattered photons. A second portion of scattered photons corresponding to higher energy photons may preferentially pass through the first detection layer 250 without significant absorption, and then reach the second detection layer 260. The second portion of scattered photons may be preferentially absorbed and detected by the second detection layer 260, so that the second detection layer 260 outputs a second signal corresponding to the second portion containing higher energy photons. Furthermore, material may be placed between the first and second detection layers to accentuate the difference in the photon spectra reaching the first and second detection layers. The material may be photon absorption material preferentially absorbing low energy photons.

In other embodiments, the radiation detector 230 may include more than two detection layers, such as three, ten or a hundred detection layers, so that the radiation detection can detect photon energy specifically within more than two energy ranges. The number of energy ranges may be determined based on a plurality of variables, such as the specific requirement of the application, the sensitivity of the radiation detector, and the intensity of the scattered photons.

Figure 2C:
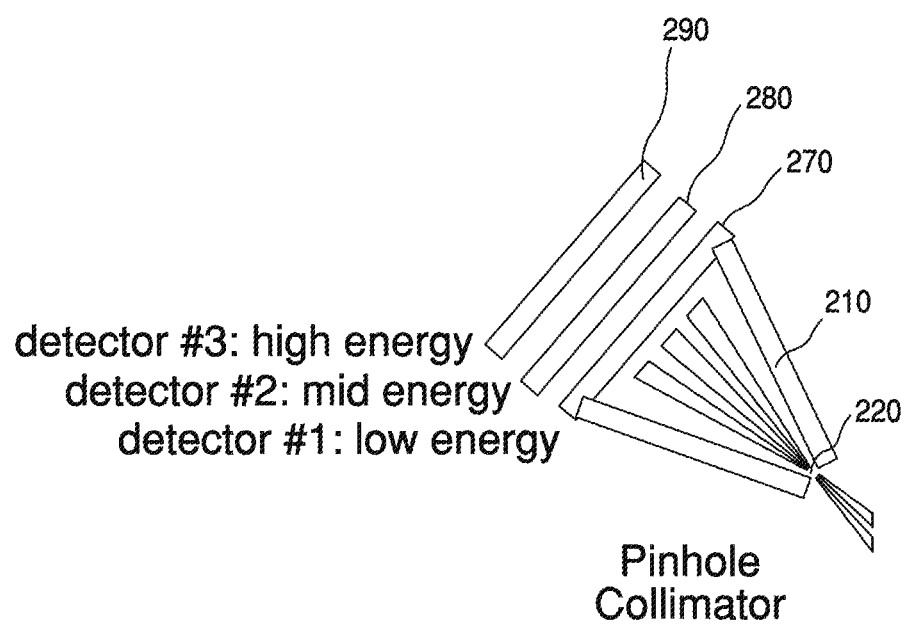
FIG. 2C illustrates another embodiment of the radiation detector including three detection layers for performing energy-resolved scatter imaging during radiation therapy.

FIG. 2C shows an embodiment of a radiation detector 230 having three detection layers. The apparatus includes a pinhole collimator 210 with pinhole 220. The radiation detector 230 has a first detection layer 270, a second detection layer 280, and a third detection layer 290. Radiation photons with low energy is absorbed and detected by the first detection layer 270. Radiation photons with middle energy passes the first detection layer 270, and is absorbed and detected by the second detection layer 280. Radiation photons with high energy passes the first detection layer 270 and the second detection layer 280, and is absorbed and detected by the third detection layer 290.

The image controller 240 is in communication of the radiation detector 230, and is capable of receiving the electrical signals corresponding to the scattered photons detected by the radiation detector. The image controller 240 may comprise memory storing instructions and a processor in communication with the memory. When the processor executes the instructions, the processor is configured to cause the image controller to perform specific functions. In one embodiment, when the radiation detector 230 outputs the first signal corresponding to detected photons within the first energy range and the second signal corresponding to detected photons within the second energy range, the image controller 240 is capable of receiving and converting the first signal into a first image data set and the second signal into a second image data set.

The image controller 240 may be further capable of performing an image operation on image data sets. The image operation may include but is not limited to overlaying one image data set onto another image data set, multiplying every data of the image data set by a numerical factor, and subtracting one image data set from another image data set.

During Campton scattering, the energy of the scattered photons depends on the initial photon energy and the scattering angle. If the initial radiation beam includes a polyenergetic spectrum, then the resulting Compton-scattered photons are also polyenergetic. The Compton scattering may occur once, as shown as a $1^{st}$-order scattered photon in FIG. 4A. The scattered photon may undergo Compton scattering again, resulting in a multiple-order scattered photon, such as a $2^{nd}$-order, $3^{rd}$-order and $4^{th}$-order scattered photon. FIG. 4B shows one example of a $4^{th}$-order scattered photon. Each successive scattering event results in lower energy of the scattered photon.

Figure 4A:
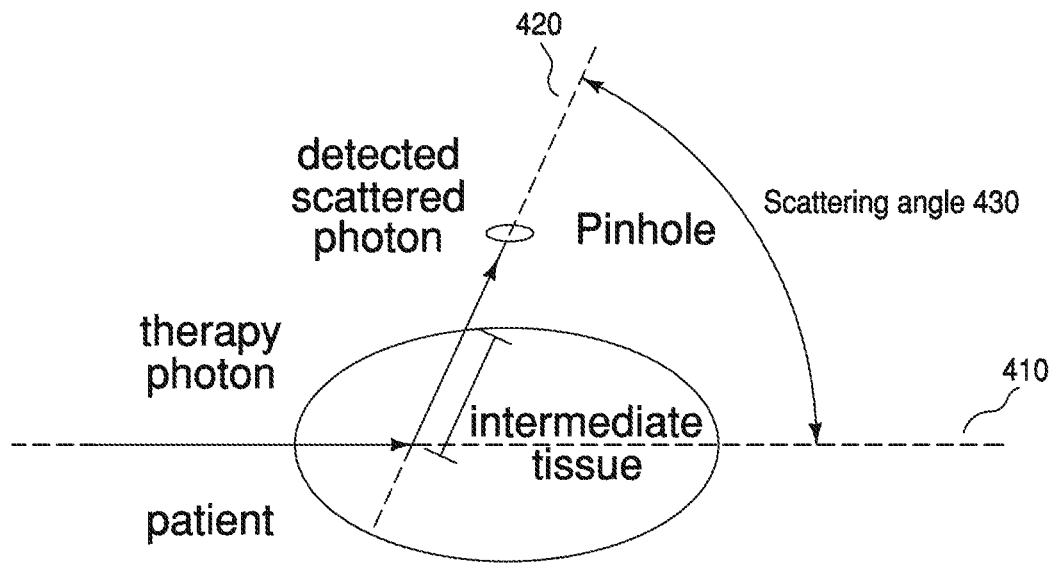
FIG. 4A is a schematic diagram of a 1$^{st}$-order scattered photon.
Figure 4B:
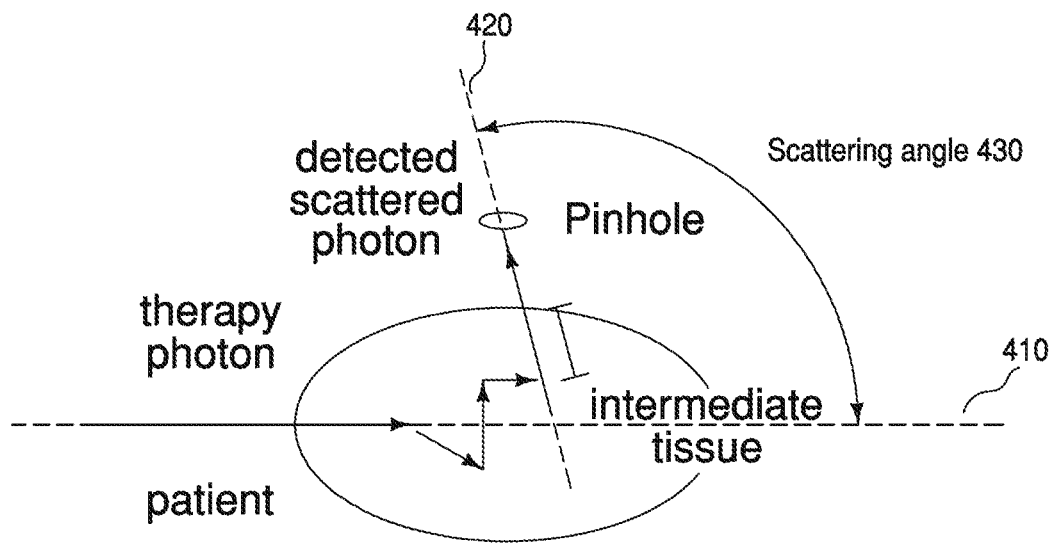
FIG. 4B is a schematic diagram of a multiple-order scattered photon.

FIG. 4A shows a scattering angle 430 for the $1^{st}$-order scattered photon. The scattering angle 430 is an angle between a first direction 410 aligned with the therapy photon in the radiation beam and a second direction 420 aligned with the scattered photon passing through the opening of the collimator. The scattering angle 430 may be adjustable between about 30° and about 150°. On average, the smaller the scattering angle 430, the higher the energy of the scattered photons and also the larger fraction the $1^{st}$-order scattering contributes to the total scattered photons passing the opening of the collimator.

Scatter imaging is advantageous for real-time radiation therapy image guidance. By collecting and analyzing scatter images, we may ensure that the tumor is within the treatment field, which allows for sparing of normal tissue and improved radiation therapy outcomes. Scatter imaging is advantageous to other real-time image-guidance techniques, for example, kilovoltage imaging or portal electronic portal imaging devices (EPID) imaging, because scatter imaging is real-time and expected to have higher contrast, leading to higher sensitivity, than absorption based methods. Furthermore, there is no additional dose associated with scatter imaging, multiple images may be simultaneous collected from various angles through multiple radiation detectors, and no fiducials are required. During scatter imaging, the position of a collimator may be versatile and may be anywhere outside of the radiation beam path.

The Compton-scatter probability and scattered photon energy can be analytically calculated based on the incident photon energy, the scattering angle, and the electron density of the material. Since Compton-scattered radiation (photons) carry information about the irradiated material, the formed scatter image can be used to distinguish the irradiated material.

For example, since the scatter imaging is capable of distinguishing tumor tissue from healthy tissue, scatter imaging may be used for tumor tracking. During radiation therapy, the tumor 130 may move slightly or leave the center of the radiation beam, for example, due to breathing motion. The scatter imaging may detect this movement and further adjust either radiation beam or the patient to bring back the tumor at the center of the radiation beam. Although kV imaging is currently used for tumor tracking, kV imaging have a few significant problems, which may include that kV imaging delivers extra dose to the patient; the view of kV imaging is constrained either by its ceiling/floor mounting or at 90° relative to the radiation beam; and kV imaging is a transmission technique that lacks the contrast of scatter imaging.

Figure 3A:
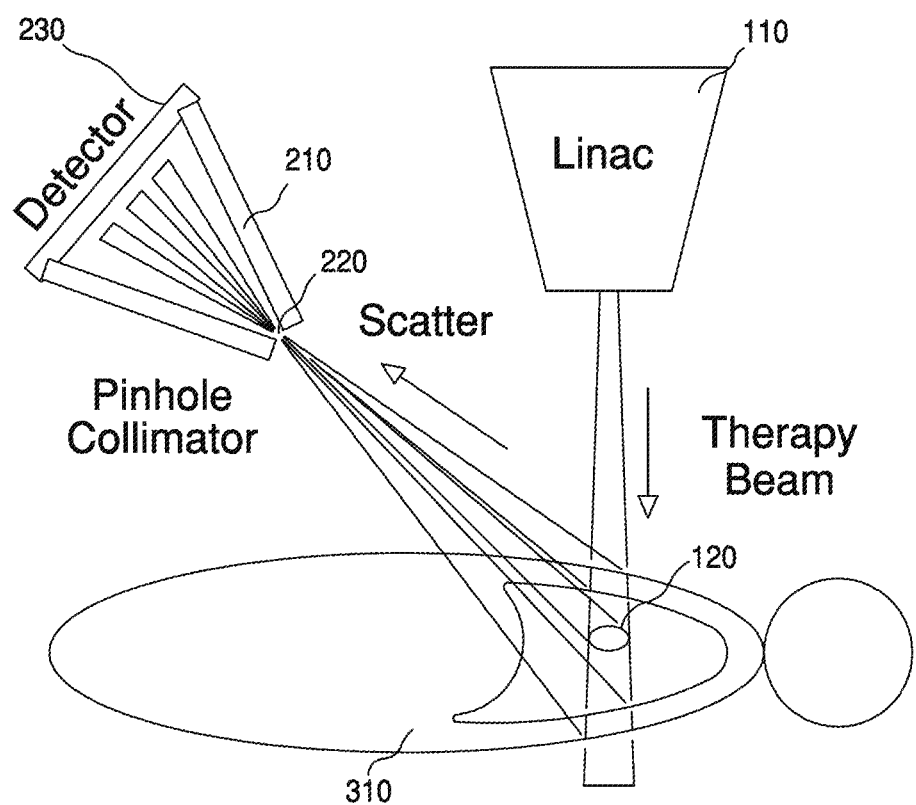
FIG. 3A is a perspective view of one embodiment of the system for performing energy-resolved scatter imaging during radiation therapy.

One embodiment is shown in FIG. 3A. The radiation source 110 is a linear accelerator (Linac), which deliveries the radiation beam, i.e., therapy beam, upon the region 120 with or having a tumor in a patient 310. An apparatus is positioned to perform energy-resolved scatter image. The apparatus includes a pinhole collimator 210 with pinhole 220. Only a small portion of the scattered photons passes through the pinhole 220 and reaches the radiation detector 230.

Figure 3B:
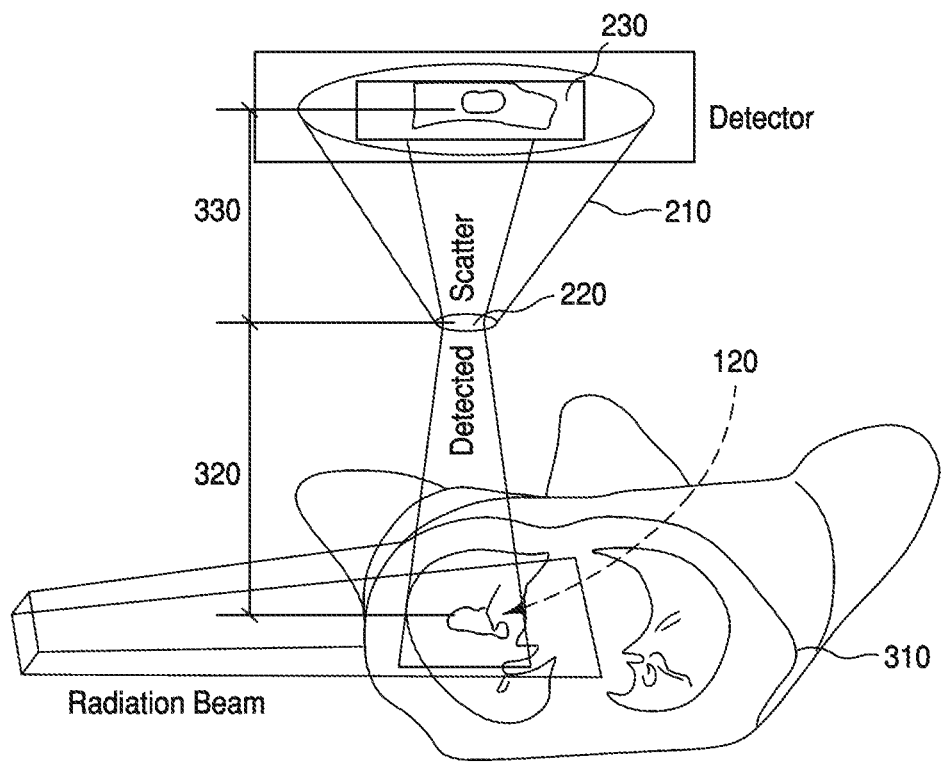
FIG. 3B is a perspective view of one embodiment of the system for performing energy-resolved scatter imaging during radiation therapy.

A perspective view of one embodiment is shown in FIG. 3B. The patient 310 is positioned on a structure configured to position and support the patient. The radiation beam is delivered from a radiation source upon a region 120 with or having a tumor in the patient 310. A portion of the scattered radiation passing through an opening 220 of a pinhole collimator 210. Due to the restriction of the opening 220 (pinhole in the embodiment), a scatter image of the region with or having the tumor is formed on the radiation detector 230.

In one embodiment, the radiation detector 230 and the collimator 210 are positioned to achieve a certain magnification ratio of the scatter image. In FIG. 3B, the opening 220 of the collimator is positioned at a first preset distance 320 away from the region 120 with or having the tumor, and the radiation detector 230 is positioned at a second preset distance 330 away from the opening 220 of the collimator. The magnification ratio is the ratio of the second preset distance 330 divided by the first preset distance 320. The first and second preset distances can be any practical lengths suitable for scatter imaging, for example, between about 5 and about 50 cm. The first and second preset distances can be the same, for example 18.5 cm, so that a magnification ratio of 1 is achieved. By way of non-limiting example, the optimal magnification ratio may be between about 0.5 and about 2.

The energy of the scattered photon depends on the scattering angle. When a high energy scattered photon is detected, a low angle scattering interaction may be assigned to the high energy scattered photon. A spatial mapping based on the resolved energy of the may be achieved by performing energy-resolved scatter imaging.

In one embodiment when the radiation therapy uses a monoenergetic therapy radiation beam, for example, using a $^{60}$Co source teletherapy unit. In this embodiment, the collimator may be removed or the opening of the collimator may be wide open since the spatial localization of the scattered photon is determined by the detected scattered photon energy.

In another embodiment when the radiation therapy uses a polyenergetic therapy beam, the scattered photo energy depends on many variables, which include but are not limited to scattering angle and initial radiation photon energy. During energy-resolved scatter imaging, the scattered photons within a highest energy range may be assigned to low-angle primary scattering. The scattered photons within a lowest energy range may be assigned to multiple-order scattering.

FIGS. 5A-5D shows simulated energy-resolved scatter images. In this embodiment, the radiation detector 230 is configured to resolve the scattered photon energy into three energy ranges: the low energy range of smaller than 190 keV; the middle energy range of larger than or equal to 190 keV and smaller than or equal to 325 keV; and the high energy range of larger than 325 keV. 1 keV equals to $1 \times 10^3$ eV.

Figure 5A:
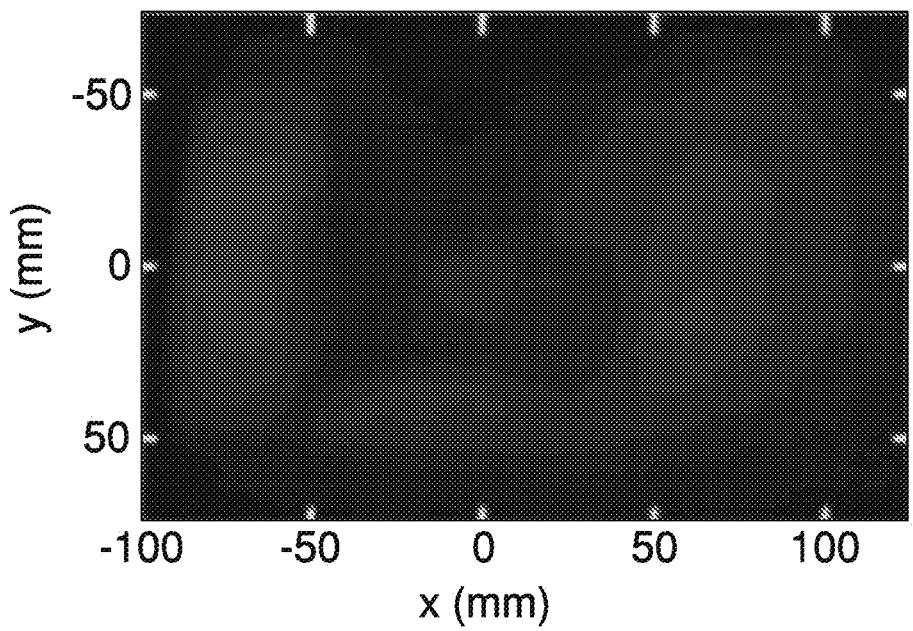
FIG. 5A is an energy-resolved scatter image in the red channel corresponding to the scattered photons within the low energy range (≤190 keV).

FIG. 5A shows the energy-resolved scatter image in the red channel corresponding to the scattered photons within the low energy range (<190 keV). The image controller 240 is configured to receive first signal corresponding to the scattered photons within the low energy range (<190 keV) from the radiation detector, convert the first signal into a first image data set, and assign the first image data set into a red color channel.

Figure 5B:
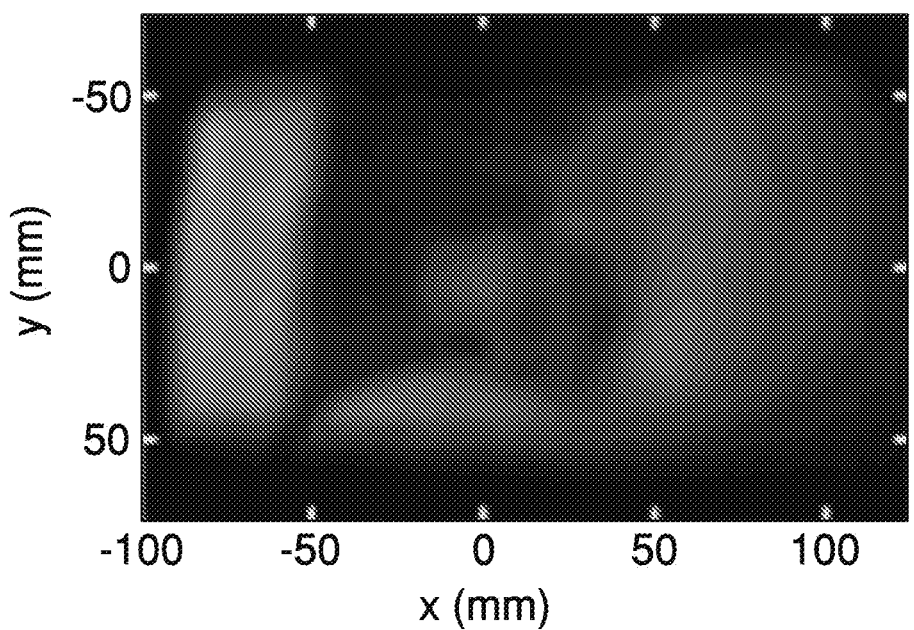
FIG. 5B is an energy-resolved scatter image in the green channel corresponding to the scattered photons within the middle energy range (≥190 keV and ≤325 keV).

FIG. 5B shows the energy-resolved scatter image in the green channel corresponding to the scattered photons within the middle energy range (≥190 keV and ≤325 keV). The image controller 240 is configured to receive second signal corresponding to the scattered photons within the middle energy range (≥190 keV and <325 keV) from the radiation detector, convert the second signal into a second image data set, and assign the second image data set into a green color channel.

Figure 5C:
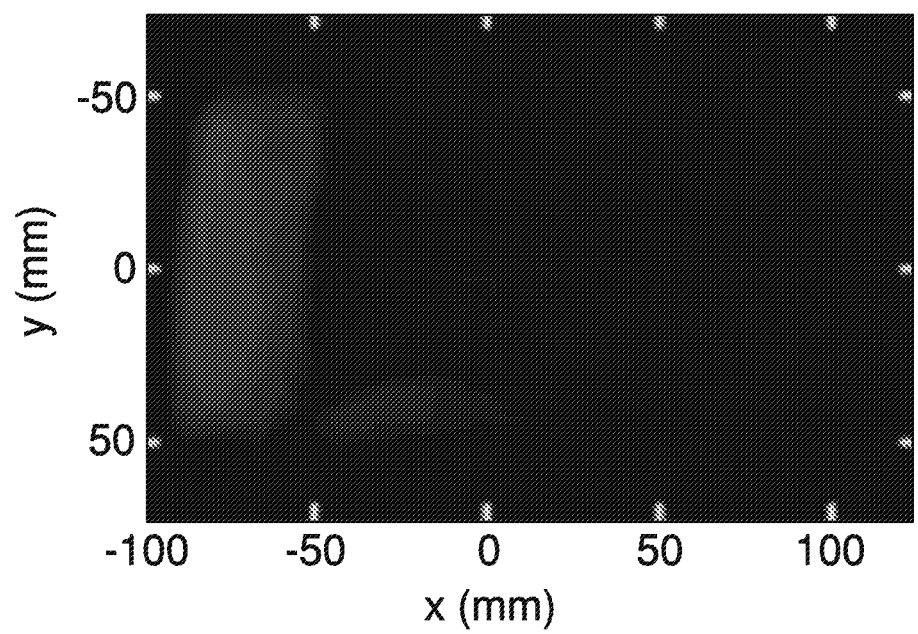
FIG. 5C is an energy-resolved scatter image in the blue channel corresponding to the scattered photons within the high energy range (>325 keV).

FIG. 5C shows the energy-resolved scatter image in the blue channel corresponding to the scattered photons within the high energy range (≥325 keV). The image controller 240 is configured to receive third signal corresponding to the scattered photons within the high energy range (>325 keV) from the radiation detector, convert the third signal into a third image data set, and assign the third image data set into a blue color channel.

Figure 5D:
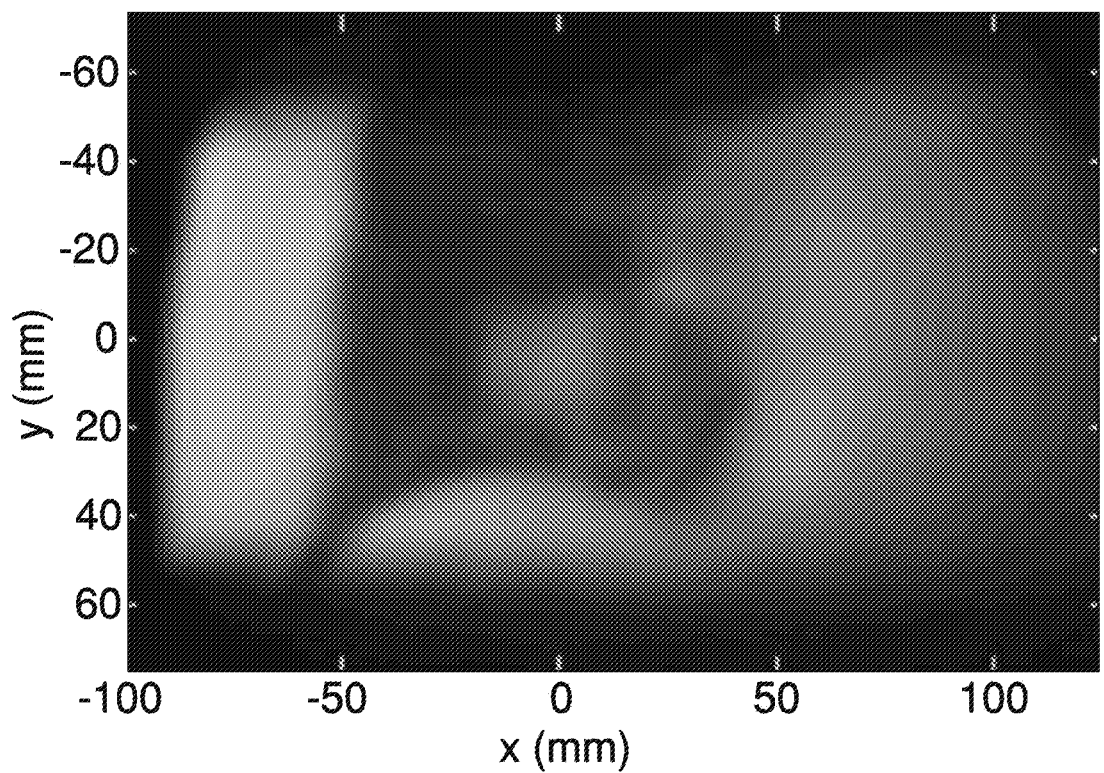
FIG. 5D is the energy-resolved scatter image in three color channels corresponding to the scattered photons within the three different energy ranges.

FIG. 5D shows the energy-resolved scatter image in three color channels corresponding to the scattered photons within the three different energy ranges. The image controller 240 is configured to overlay the first, second, and third image data sets together to obtain the energy-resolved scatter image in three color channels. The overlaying operation may be performed by summing every image data set in each color channel, respectively. As the scattering angle increases, the scattered photon energy decreases. Thus, considering the radiation beam is delivered from negative x-axis towards positive x-axis, the scattered photons from the front (the left side in FIGS. 5A-5D) have the higher energy on average, while the scattered photons from the back end (the right side in FIGS. 5A-5D) have lower energy on average. Lower energy scattered photons appears at the top and bottom edges in FIG. 5D beyond an irradiating field due to multiple-order scattering process.

In another embodiment, energy-resolved scatter imaging is used to identify tissue types. Since different materials have different energy-dependent absorption coefficients. As shown in FIG. 4A for the $1^{st}$-order scattered photon and FIG. 4B for the multiple-order scattered photon, the scattered photons pass through the intermediate tissue after their final scattering interaction before passing through the collimator and reaching the radiation detector. By analyzing energy-resolved scatter images, the difference of different materials in energy-dependent absorption may be used to identify tissue type.

In one embodiment, the contract of energy-resolved scatter imaging may be improved by administrating a contrast agent. The contrast agent may include but is not limited to iodine. Iodine has a strong absorption at radiation photons with energy lower than 100 keV due to its large photoelectric cross section. When iodine is injected into a patient before radiation therapy, iodine may preferentially accumulate in the tumor due to the leaky tumor vasculature. During radiation treatment, the scattered photons within a low energy range may exhibit lower intensity in the region of the tumor due to the absorption of low energy photons by the iodine. The scattered photons within a high energy range may exhibit intensity comparable to a typically dense tissue. By comparing the intensity of scattered photons within the low and high energy ranges, the presence of iodine may be detected, leading to locate the tumor position.

Figure 6A:
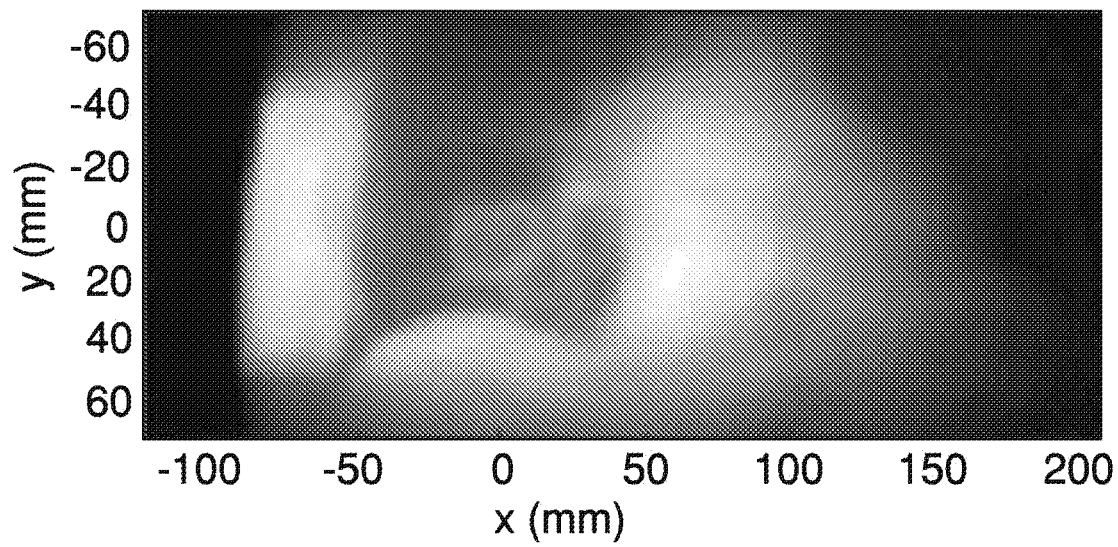
FIG. 6A is an energy-resolved scatter image corresponding to the scattered photons within the low energy range (<100 keV).
Figure 6B:
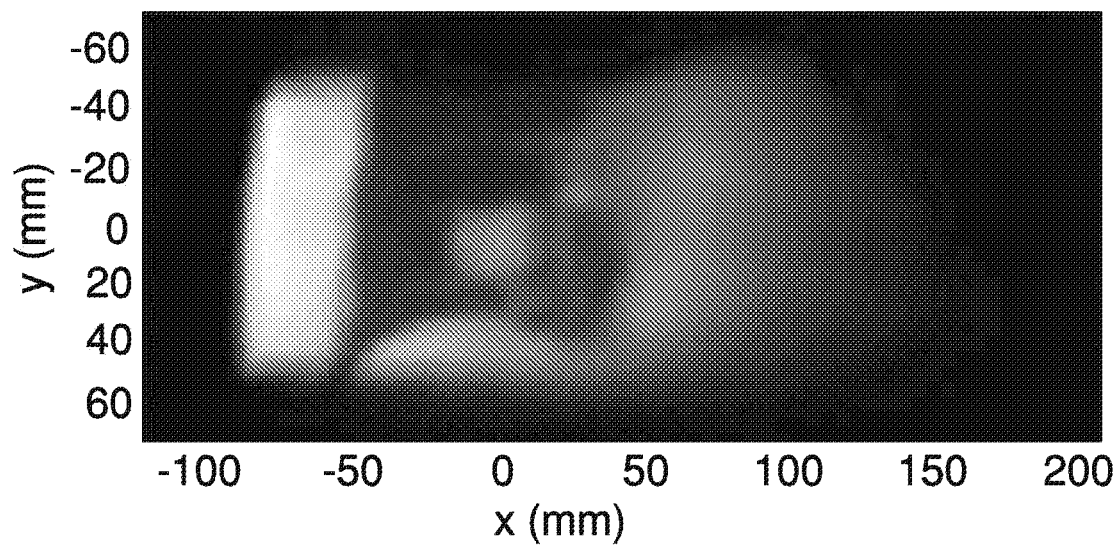
FIG. 6B is an energy-resolved scatter image corresponding to the scattered photons within the high energy range (≥100 keV).
Figure 6C:
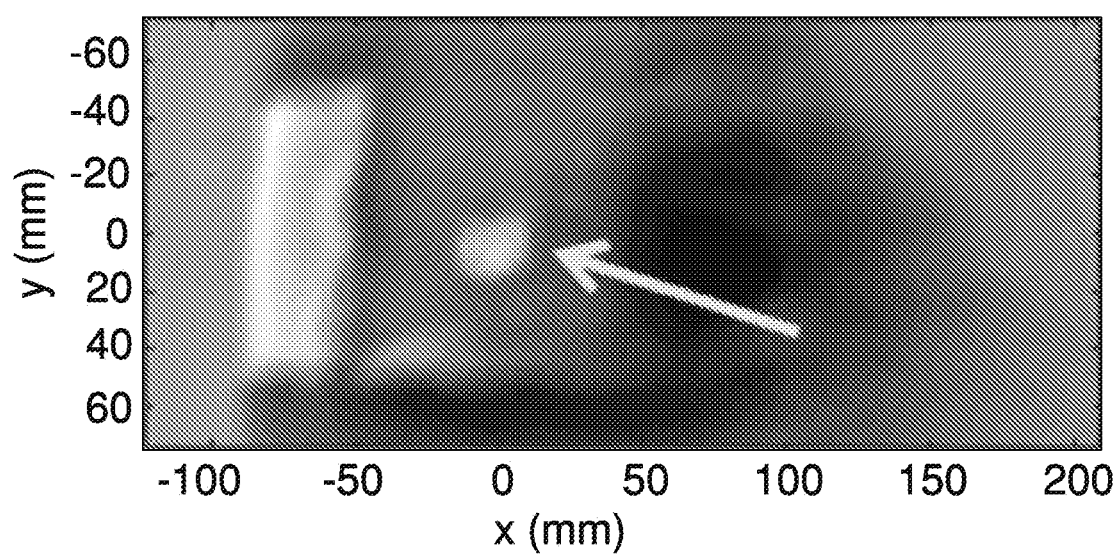
FIG. 6C is the energy-resolved scatter image of a weighted difference of the intensity of the scattered photons within the high and low energy ranges.

FIGS. 6A-6C shows simulated energy-resolved scatter images to locate a tumor after iodine accumulation. In this embodiment, the radiation detector 230 is configured to resolve the scattered photon energy into two energy ranges: the low energy range of smaller than 100 keV; and the high energy range of larger than or equal to 100 keV.

FIG. 6A shows the energy-resolved scatter image corresponding to the scattered photons within the low energy range (<100 keV). The image controller 240 is configured to receive first signal corresponding to the scattered photons within the low energy range (<100 keV) from the radiation detector and convert the first signal into a first image data set. Since the tumor with iodine preferentially absorbs scattered photons within the low energy range relative to surrounding normal tissue, the tumor appears darker with lower intensity.

FIG. 6B shows the energy-resolved scatter image corresponding to the scattered photons within the high energy range (≥100 keV). The image controller 240 is configured to receive second signal corresponding to the scattered photons within the high energy range (≥100 keV) from the radiation detector and convert the second signal into a second image data set.

FIG. 6C shows the energy-resolved scatter image obtained from calculating a weighted difference of the first and second image data corresponding to scattered photons within the high and low energy ranges, respectively. The image controller 240 is configured to calculate the weighted difference of the first image data set and second image data set to obtain the energy-resolved scatter image data set. For example, the image controller 240 multiplies the first image data set by a first numerical factor to obtain a third image data set, multiplies the second image data set by a second numerical factor to obtain a fourth image data set, and subtracts the third image data set from the fourth image data set to obtain the energy-resolved scatter image data set. The tumor position is identified and marked with an arrow. The contrast of the energy-resolved scatter image is significantly improved over other methods through the combination of iodine contrast enhancement and energy-resolved capability. In another embodiment, the first and second numerical factors are chosen so that the total intensity of the third image data set is similar to the total intensity of the fourth image data set.

Figure 7:
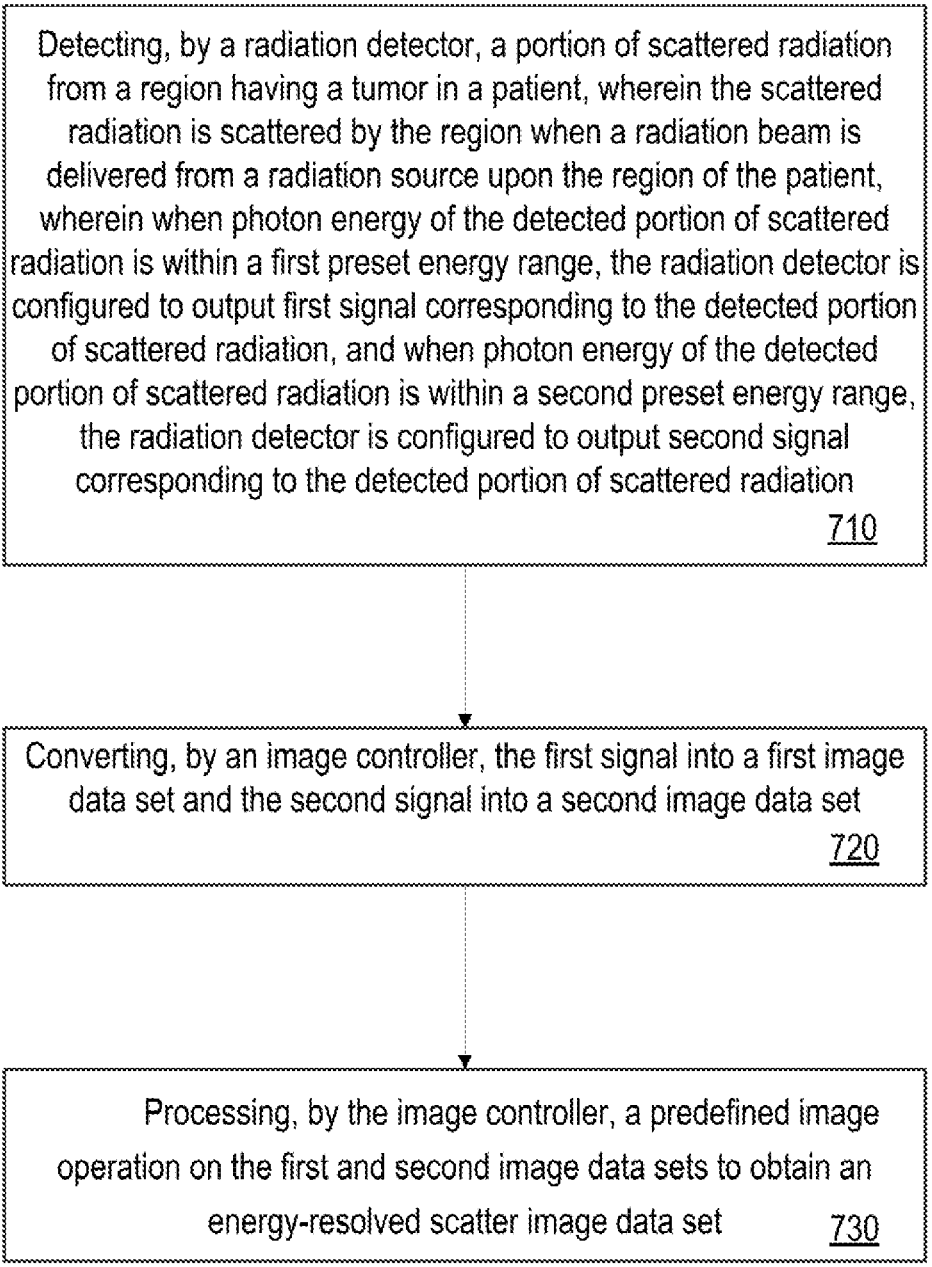
FIG. 7 is a flow diagram of a method for performing energy-resolved scatter imaging during radiation therapy upon a patient.

FIG. 7 shows a method for performing energy-resolved scatter imaging during radiation therapy upon a patient. The method includes step 710: detecting, by a radiation detector, a portion of scattered radiation from a region with or having a tumor in a patient, wherein the scattered radiation is scattered by the region when a radiation beam is delivered from a radiation source upon the region of the patient. When photon energy of the detected portion of the scattered radiation is within a first energy range, the radiation detector is configured to output first signal corresponding to the detected portion of the scattered radiation. When photon energy of the detected portion of the scattered radiation is within a second energy range, the radiation detector is configured to output second signal corresponding to the detected portion of the scattered radiation. The first energy range is different from the second energy range. In one embodiment, the first energy range may have a portion of energy range overlapping with the second energy range, but the first energy range is not the same as the second energy range.

The method also include step 720: converting, by an image controller, the first signal into a first image data set and the second signal into a second image data set. Furthermore, the method include step 730: processing, by the image controller, a predefined image operation on the first and second image data set to obtain an energy-resolved scatter image data set.

Figure 8A:
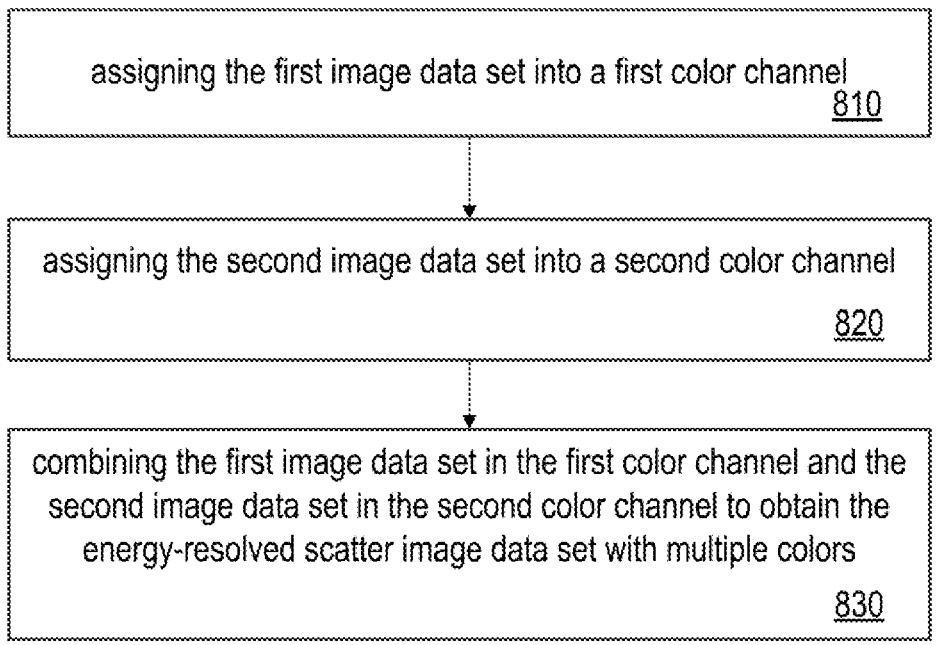
FIG. 8A is a flow diagram of one embodiment of processing first and second image data sets to obtain the energy-resolved scatter image data set.

FIG. 8A shows one embodiment for processing the predefined image operation on the first and second image data sets to obtain the energy-resolved scatter image data set. The embodiment includes step 810: assigning the first image data set into a first color channel; step 820: assigning the second image data set into a second color channel; and step 830: combining the first image data set in the first color channel and the second image data set in the second color channel to obtain the energy-resolved scatter image data set with multiple colors.

Figure 8B:
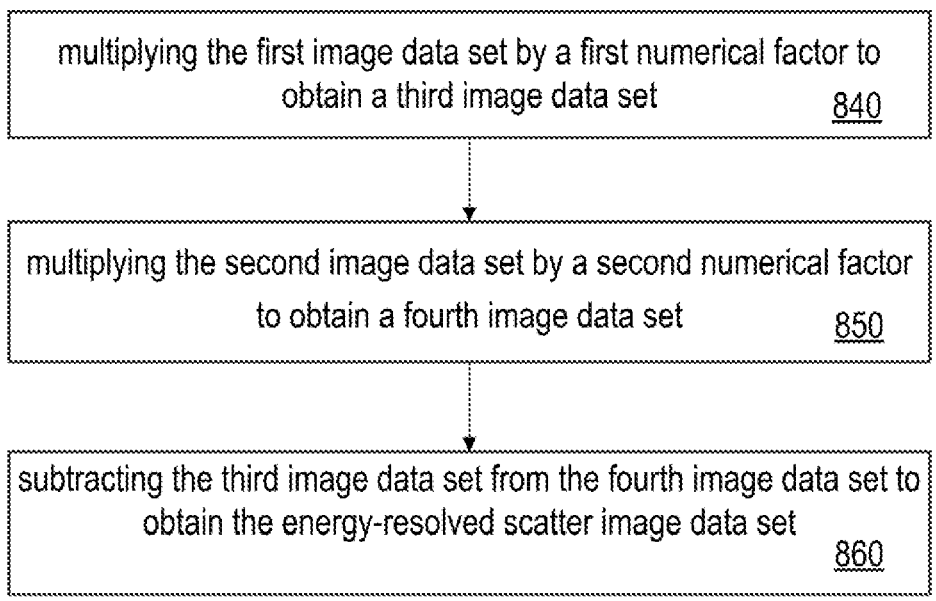
FIG. 8B is a flow diagram of one embodiment of processing first and second image data sets to obtain the energy-resolved scatter image data set.

FIG. 8B shows another embodiment for processing the predefined image operation on the first and second image data sets to obtain the energy-resolved scatter image data set. The embodiment includes step 840: multiplying the first image data set by a first numerical factor to obtain a third image data set; step 850: multiplying the second image data set by a second numerical factor to obtain a fourth image data set; and step 860: subtracting the third image data set from the fourth image data set to obtain the energy-resolved scatter image data set.

In one embodiment, an analytical method may be used to simulate scatter imaging and energy-resolved scatter imaging. By collimating the photons scattered when a megavoltage therapy beam interacts with the patient, a Compton-scatter image may be formed without the delivery of extra dose. To characterize and assess the potential of the technique, an analytical model for simulating scatter images was developed and validated against Monte Carlo (MC). For three phantoms, the scatter images collected during irradiation with a 6 MV FFF therapy beam were simulated with analytical and MC methods. Images, profiles, and spectra were compared for different phantoms and different irradiation angles. The images were analyzed based on their energy-dependence, contrast, and the fraction of photons from multiple scattering. The proposed analytical method simulates accurate scatter images up to 1000 times faster than MC. For the considered lung tumor CT phantom, the contrast is high enough to clearly identify the lung tumor in the scatter image. For a detector placed at 90° relative to the 6 MV FFF treatment beam, the scattered photons' spectrum peaks at 140-220 keV and extends up to 780 keV. The high energy photons primarily originate at the front face of the phantom. For an ideal 5 mm diameter pinhole collimator placed 18.5 cm from isocenter, 10 cGy of deposited dose is expected to generate an average $1\times10^3$ photons per $mm^2$ at the detector. Of these photons, 40-50% are the result of multiple scattering. Increasing the angle between source and detector increases the average energy of the collected photons. With the analytical method, real-time tumor tracking may be possible through comparison of simulated and acquired patient images.

Introduction

The most important photon interaction for megavoltage therapy photon beams is Compton-scattering, which dominates for low atomic number (Z<8) materials over the ~0.026-24 MeV energy range. During Compton-scattering, an incident photon scatters into a different direction with a longer wavelength, and its lost energy is contributed to the kinetic energy of an electron. The other scattering process—coherent scattering—is negligible over the considered energy range, and any further mention of scattering is in reference to Compton-scatter. The scatter probability and scattered photon energy can be analytically calculated based on the incident photon energy, the scattering angle, and the electron density of the material. An image may be formed by identifying the origin of the scattered photons through proper collimation[1-4], by mapping energies to spatial coordinates[5,6], with a Gamma camera[7], or through coded-aperture techniques[8].

A number of applications have been proposed for scatter images. Because the intensity of the image is proportional to electron density, researchers proposed[9] and showed[1-4] that scatter images may be used to create volumetric electron density maps of 3D objects and tissues, although steps must be taken to reduce the contribution from multiple scattering[2] and correct for attenuation[1,10,11]. The high fluence (and resulting dose) required for these measurements and the development of kilovoltage computed tomography (CT) made scatter electron density mapping obsolete[12]. Because the intensity is dependent on the number of incident photons, scatter imaging may also provide a method for quantitatively measuring the delivered 3D dose[7].

More recently, scatter imaging has been proposed as a possible technique for real-time tracking of tumor motion during radiotherapy treatment[13,14]. Because photons are scattered in all directions, scatter imagers can be placed at many points surrounding a patient to provide imaging at different viewing angles. Rather than using an external kV X-ray source[13], the focus of this work is to analyze the images generated by collecting photons scattered from the treatment beam itself[14]. Because the therapeutic beam is the source of the scattered photons, no additional imaging dose is deposited. Scatter imaging is particularly applicable to hypofractionated treatments because millimeter accuracy and tumor motion corrections are required, and the large deposited dose may generate images with adequate signal-to-noise ratios for real-time guidance.

Here, we develop an analytical technique for simulating scatter images. The purpose is two-fold. The first is to develop a simulation method that is computationally faster than the previously-used Monte Carlo (MC) simulations. A fast, accurate simulation method will allow for faster development and assessment of the Compton-scatter imaging technique. In addition, scattering affects other techniques such as SPECT and PET imaging[15,16]. Development of an analytical scatter modeling technique may improve reconstruction algorithms for these different imaging modalities. Second, by attempting to model scatter images, the underlying physical processes and image features can be better understood.

The simulation method described here assumes that only photons passing through a hole (an ideal pinhole collimator) located above the phantom reach the detector. Combined with the knowledge that photons travel along straight lines, an image may be formed by imposing this pinhole restriction.

Methods: Analytical Compton-Scatter Image Simulation

The analytical scattered images were calculated in a multi-step process: source photon deposition, Compton-scattering, and signal photon collection. A general description of the algorithm is given here (and in FIG. 9) before each step is described in more detail below. First, ray-tracing is used to determine the number of source photons that reach each irradiated voxel within the CT volume. Next, based on the number of incident photons, two quantities are calculated and associated with each voxel: the number and spectrum of photons primary (n=1) Compton-scattered into the solid angle of the pinhole ($\Omega_{pin}$) and the total number and spectrum of photons primary scattered in all directions ($\Omega_{4\pi}$). To calculate multiple scattering (n>1), the total photons ($\Omega_{4\pi}$) from the primary scattering are propagated in all directions through kernel convolution/superposition. This propagation is followed by a scattering step in which the total number of scattered photons are used to seed the next round of propagation, and the fraction of the total photons scattered into the pinhole solid angle ($\Omega_{pin}$) is recorded for each voxel. The kernel propagation and scattering is repeated five times ($2^{nd}$-through $6^{th}$-order scattering). Finally, in the last step, the higher order and the primary scattered $\Omega_{pin}$ photons from each voxel are attenuated along collection rays emanating to the pinhole and summed to give the scatter image for an ideal pinhole collimator and detector combination.

The coordinate system (see FIG. 9) is defined in relation to a head-first, supine patient lying on a treatment couch such that the x, y, and z unit vectors correspond to patient right-to-left, anterior-to-posterior, and inferior-to-superior axes, respectively. Here, the treatment couch position is fixed so that a gantry rotation moves the beam around the z axis. The pinhole is always positioned along the –y axis (at gantry angle, $\theta_g=0°$).

Figure 9:
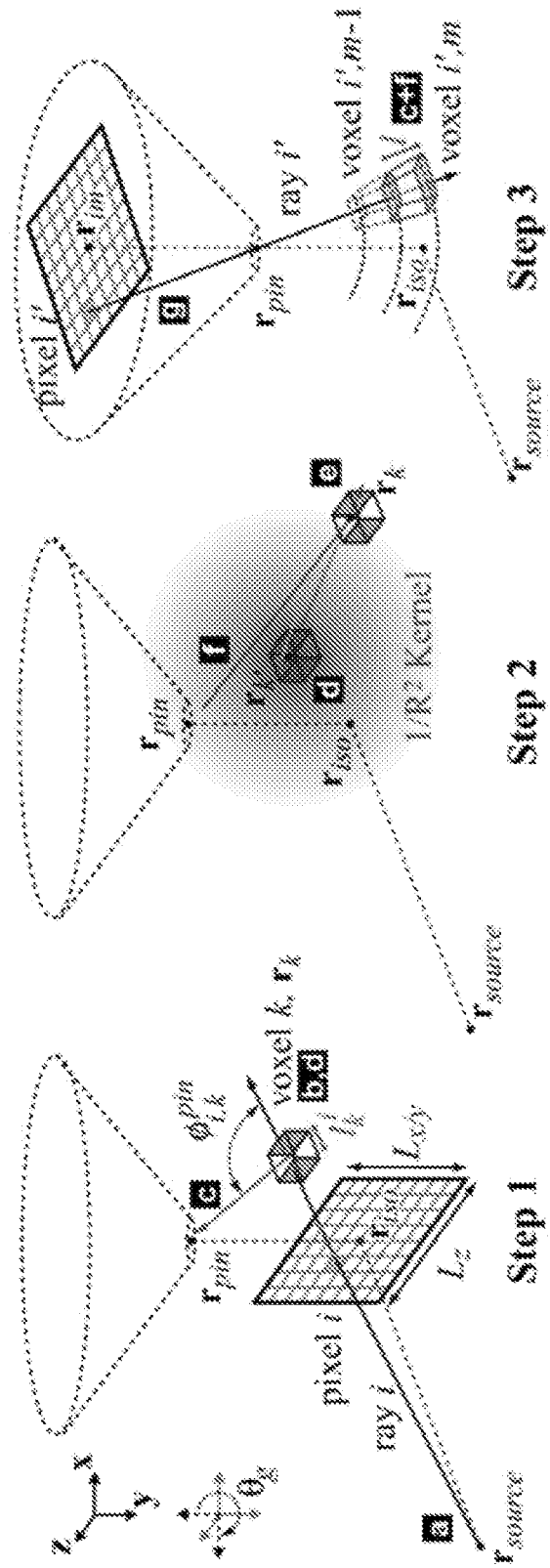
FIG. 9 illustrates an analytical simulation method.

FIG. 9 shows that the analytical simulation method is described with an illustration. In Step 1, each ray (indicated by a [$N_{0,\Omega i}^j$ photons], of solid angle $\Omega_i$) is traced through the phantom and attenuated. The number of photons reaching each voxel (b [$N_{0,\Omega i}^j(r_k)$]) is scattered. The number and energy of photons scattered towards the pinhole is recorded (c [$N_{0,\Omega pin}^{j}(r_k)$]). The total number of n=1 scattered photons and their average spectrum (d [$N_{n-1,\Omega 4\pi}(r_{k'})$ photons, spectrum $N_{n-1,\Omega 4\pi}^{j,norm}$]) are used as the starting point of Step 2, in which propagation of d is modeled with a convolution/superposition algorithm. The total number and spectrum of photons that scatter from the n−1 round (into the n round, e [$N_{n,\Omega 4\pi}(r_k)$ photons, spectrum $N_{n,\Omega 4\pi}^{j,norm}$]) is used to seed progressive rounds, while the fraction of photons scattered towards the pinhole is recorded (f[$N_{n,\Omega pin}^{j}(r_k)$]). Finally, all of the photons scattered by each voxel are summed (c+f) in Step 3, and attenuated by tracing along rays that pass through the pinhole to each detector pixel (g [$N_i^j$]).

Method: Source Photon Deposition

Figure 10:
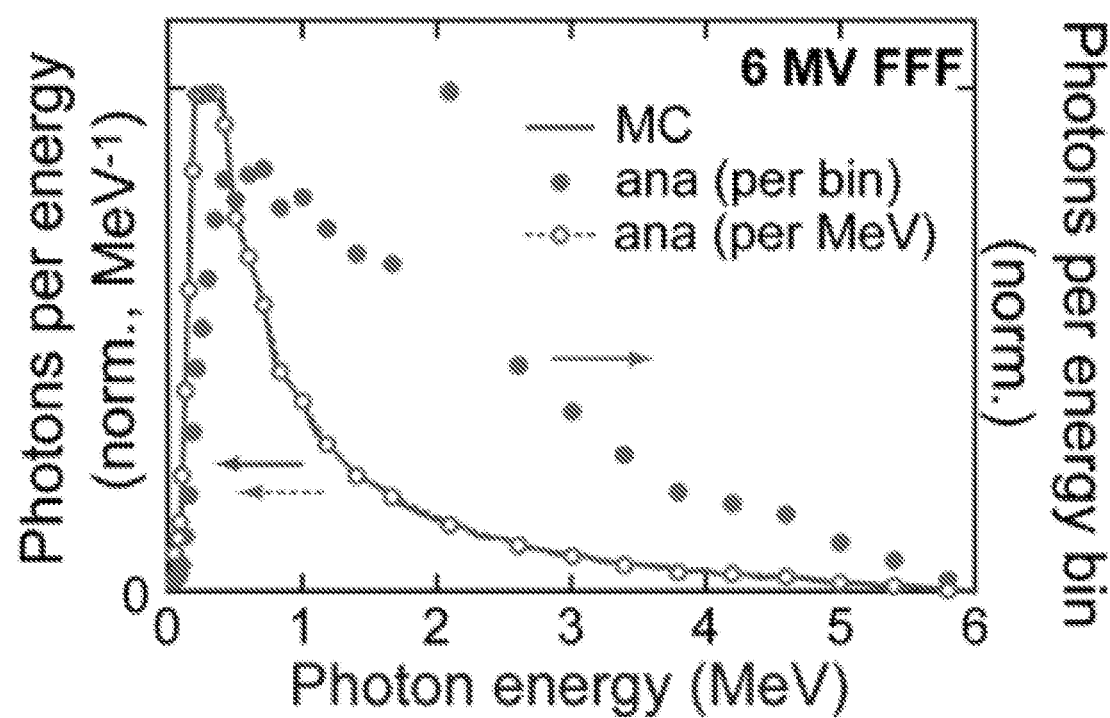
FIG. 10 shows a radiation beam spectrum and source photons per energy bin.

FIG. 10 shows that the 6MV FFF treatment beam source spectrum (used for the MC simulations) and source photons per energy bin (analytical simulations) are shown. To reduce the computational time and memory requirements, non-uniform source photon energy bins ($N_0^j$) were used (solid dots, right axis). When divided by the energy bin width (photons/bin→photons/MeV), the analytical source photon distribution spectrum matches the desired 6 MV FFF spectrum. The energy bin centered at 2.1 MeV has a larger width—and amplitude—than the surrounding bins.

An isotropic point source is assumed and defined at $r_{source}$. Field size is defined and centered at the isocenter, $r_{iso}$, as a rectangle of dimensions $L_{x/y} \times L_z$ normal to the vector ($r_{iso}-r_{source}$). $L_z$ is the field length along the z axis while $L_{x/y}$ is the length along the $\cos(\theta_G)$ x+$\sin(\theta_G)$ y direction. The rectangular field is split into rectangular pixels. Rays are generated that originate at $r_{source}$ and travel through the center of each field pixel. These beamlet rays carry the source photons through the attenuating CT volume. Each ray carries $N_{0,\Omega i}$ photons, where the 0 subscript indicates that the photons originate at the source, and $\Omega_i$ represents the solid angle of field pixel (and associated ray) i. The energy of these photons is distributed discretely over the source spectrum such that summing over the j energy bins gives $$N_{0,\Omega i} = \sum_j N_{0,\Omega i}^j.$$

The spectrum of source photons is shown in FIG. 10, which is a typical output spectrum for a Truebeam 6 MV flattening-filter-free (FFF) therapeutic x-ray beam. The number of photons carried by each ray ($N_{0,\Omega i}$) is proportional to the solid angle represented by each ray. The total number of photons in the full beam is normalized to 1. Thus the number of photons collected per pixel in the final scattered image represents the number expected per source photon in an irradiating field of size $L_{x/y} \times L_z$. Multiplying by the beam area gives the number of photons expected per source photon fluence. The photon fluence ([photons/m$^2$]) for ray i reaching voxel k at a distance R from $r_{source}$ (R=|$r_k - r_{source}$|) is given by $N_{0,\Omega i}/\Omega_i R^2$. Because each ray carries a number of photons proportional to its represented solid angle, the fluence of each ray is the same as the fluence for the total beam, $N_0/\Omega_0 R^2$.

Each ray i is traced through the CT volume, and the interaction length, $l_i^k$[m], with each CT voxel k is calculated[17]. The source photons of energy j that reach voxel k is then given by:

$$N_{0,\Omega i}^j(r_k) = N_{0,\Omega i}^j \exp\left[\sum_{m=1}^{M} -\mu_j(r_m)l_i^m\right] \quad (1)$$

where the sum represents the cumulative attenuation of the photons at energy j over the pixels m (=1, 2, ..., M) that ray i intersects before reaching the pixel of interest, k. Along its path, the ray intersects with M voxels before reaching voxel k. $\mu_j(r_m)$ is the attenuation coefficient [m$^{-1}$](described below) for voxel m at energy j.

By allowing the rays to pass completely through the CT volume, a transmission image can be calculated based on Eq. (1).

Method: Compton-Scattering

The pinhole position, $r_{pin}$, is in the same xy plane as the source and isocenter, and is 18.5 cm from the isocenter with the vector between pinhole and isocenter oriented 90° from the source-isocenter vector, unless otherwise noted. The pinhole area is calculated using a 5 mm diameter.

As is shown below and previously[11,18-20], multiple-order Compton-scattering must be considered. Primary scattering generates some photons that undergo secondary scattering that in turn may successively undergo higher-order scattering. Thus, for each considered scattering order n, two quantities are calculated: $N_{n,\Omega pin}^j(r_k)$, the number of photons of energy j scattered by voxel k into the solid angle subtended by the pinhole, and $N_{n,\Omega 4\pi}(r_k)$, the total number of photons (of all energies) scattered by voxel k into all directions. $N_{n,\Omega pin}^j(r_k)$ is recorded and cumulatively summed after each scattering round n so that the image may be generated in the final step, while $N_{n,\Omega 4\pi}(r_k)$ is used to seed the next wave of scattering. The primary pinhole-scattered photons $N_{1,\Omega pin}^j(r_k)$ are explicitly calculated using ray-tracing. To reduce memory requirements and increase computational speed, a generalized isotropic approximation is used to calculate multiple-order scattering.

Primary Compton-Scattering in the Direction of the Pinhole

For each irradiated voxel, the solid angle subtended by the pinhole relative to the voxel, $\Omega_k^{pin}$, is calculated. For each ray and intersected voxel, the Compton-scattering angle ($\pi$ minus the angle between source-voxel-pinhole), $\phi_{i,k}^{pin}$, is calculated. For each energy j in the source photon spectrum, voxel k, and ray i, the pinhole-scattered photon energy [MeV]:

$$hv'_{i,j,k} = \frac{hv_j}{1 + \alpha_j(1 - \cos\phi_{i,k}^{pin})}, \tag{2}$$

and pinhole-scattered Compton cross section [m² sr⁻¹ per electron]:

$$\frac{d_e\sigma_{i,j,k}^{pin}}{d\Omega_\phi} = \frac{r_0^2}{2}\left(\frac{hv'_{i,j,k}}{hv_j}\right)^2\left(\frac{hv_j}{hv'_{i,j,k}} + \frac{hv'_{i,j,k}}{hv_j} - \sin^2\phi_{i,j,k}^{pin}\right), \tag{3}$$

are calculated, where the classical electron radius, $r_0=2.818\times 10^{-15}$ m, and $\alpha_j=hv_j/511$ keV. The number of energy hv' photons primary scattered towards the pinhole by each pixel k from all the rays is calculated by multiplying (first term in parentheses below) the number of incident photons of energy bin j (eq. (1)) by the electron density relative to water ($\rho_e$), the electron density of water ($\rho_w$), Compton cross section (eq. (3)), the pinhole solid angle, and the interaction length between ray and voxel:

$$N_{1,\Omega pin}^{j'}(r_k) = \left(\sum_j \sum_i N_{0,\Omega i}^j(r_k)\cdot\rho_e(r_k)\rho_w \cdot \frac{d_e\sigma_{i,j,k}^{pin}}{d\Omega_\phi}\cdot\Omega_k^{pin}\cdot l_i^k\right) \tag{4}$$

$$\left(\frac{1}{\sum_i N_{0,\Omega i}^j\cdot l_i^k}\frac{N_0}{\Omega_0 R^2}V_{vox}\right).$$

Because the rays are discrete lines interacting with an ordered grid of voxels, the first parenthetical term above results in artefactual geometric patterns—aliasing—in the number of photons reaching each voxel. To correct for this streaking, the second term is included in eq. (4). Rather than use the rays to carry photons to each voxel, the rays are instead only used to determine the attenuation along the path from source to voxel. The second term in parentheses represents normalizing by the discrete (number of photons multiplied by interaction length) contribution from all rays, and replacing it with the continuous fluence, $N_0/\Omega_0 R^2$, multiplied by the voxel volume, $V_{vox}$.

Rather than tracking the resulting scattered photons based on their initial energy ($hv_j$), the scattered photons are discretely binned into energy bins j' based on their final energy given by eq. (2).

Thus, for each voxel, the number and energy of photons primary-scattered towards the pinhole are recorded, but ray-tracing to the pinhole to determine the transmitted fraction is not yet performed; this is calculated in the final step. Increasing the pinhole area results in a linear increase in the solid angle and, thus, a linear increase in the number of photons scattered into its direction.

Total Primary Compton-Scattering

To calculate the total number of photons scattered in all directions (not just towards the pinhole), the Compton cross section integrated over all angles was calculated for each incident photon of energy j:

$$_e\sigma_j = \tag{5}$$

$$2\pi r_0^2\left\{\frac{1+\alpha_j}{\alpha_j^2}\left[\frac{2(1+\alpha_j)}{1+2\alpha_j} - \frac{\ln(1+2\alpha_j)}{\alpha_j}\right] + \frac{\ln(1+2\alpha_j)}{2\alpha_j} - \frac{1+3\alpha_j}{(1+2\alpha_j)^2}\right\}.$$

Similar to eq. (4), the number of total source photons scattered by voxel k is given by summing over all the incident photon energies:

$$N_{1,k,\Omega 4\pi} = \left(\sum_j \sum_i N_{0,\Omega i}^j(r_k)\cdot\rho_e(r_k)\cdot {_e\sigma_j}\cdot l_i^k\right)\left(\frac{1}{\sum_i N_{0,\Omega i}\cdot l_i^k}\frac{N_0}{\Omega_0 R^2}V_{vox}\right) \tag{6}$$

These photons are scattered in all directions. Keeping track of the direction and energy of each scattered photon at each voxel is too memory-intensive. The spectrum of primary scattered photons only depends on the incident photons' energy. Therefore the relative, normalized spectrum summed over all possible $\phi$ (scattered in all directions) can be approximately calculated by summing the differential Compton cross section weighted by the number of photons of energy j $$N_{1,\Omega 4\pi}^{j',norm} = \frac{1}{N_{0e}\sigma_j}\sum_j\sum_{\phi=0,1,\ldots,180°}N_0^j\frac{d_e\sigma_j}{d\Omega_\phi}2\pi\sin\phi\cdot\Delta\phi \tag{7}$$

where $d_e\sigma_j/d\Omega_\phi$ is calculated by replacing $\phi_{i,k}^{pin}$ in eqs. (2) and (3) with the full range of possible scattering angles, $\phi=[0°, 180°]$, $\Delta\phi=1°$. The prefactor normalizes the result such that $$\sum_{j'} N_{1,\Omega 4\pi}^{j',norm} = 1.$$

As with eq. (4), the spectrum is discretized based on its scattered energy, hv', into energy bin j'. Eq. (7) is an approximation as it ignores beam hardening (the initial source spectrum ($N_0^j$) is assumed to reach each voxel).

Furthermore, from eq. (6) and (7), the number of primary photons scattered by voxel k in energy bin j' is given by multiplying the total scattered photons by the fraction in that energy bin:

$$N_{1,\Omega 4\pi}^{j'}(r_k) = N_{1,\Omega 4\pi}(r_k)\cdot N_{1,\Omega 4\pi}^{j',norm} \tag{8}$$

In reality, the scattered photon spectrum is anisotropic and dependent on the direction of incident and emitted radiation. For the computationally-fast kernel treatment described below, the spectrum is assumed to be isotropic.

Higher Order Compton-Scattering

With the total number of photons scattered at each voxel k' from the previous (n−1) order scattering, the scattering at voxel k in the current order n is given by:

$$N_{n,\Omega 4\pi}(r_k) = \langle_e\sigma\rangle\cdot\rho_e(r_k)\rho_w \tag{9}$$

$$\left\{N_{n-1,\Omega 4\pi}(r_{k'})\otimes K(r_k - r_{k'})\cdot V_{vox}\cdot\int_{1=r_{k'}}^{1=r_k}\langle\mu(1)\rangle r_{k-k'}^\$ d1\right\}.$$

The first term is the spectrum-weighted Compton cross section, where the triangular bracket indicate $$\langle g \rangle = \sum_j g_j N_{n-1,\Omega 4\pi}^{j,norm}.$$

The pre-bracket terms represent the likelihood that a photon will scatter at voxel k if it reaches it. The bracketed term calculates the number of photons that reach voxel k from all other voxels k'; $N_{n-1}$ is the total number of photons distributed over the full volume of voxel k', the kernel propagates these photons, and the line integral term represents the attenuation between voxels k' and k along the unit vector $r_{k-k'}{}^\$ = (r_k - r_{k'})/|r_k - r_{k'}|$ with spectrum-weighted attenuation coefficient given by $\langle \mu \rangle$. The kernel, K, only depends on the relative position between n−1 scattering voxel k' and n scattering voxel k. K is a three dimensional matrix where the value at $r_k - r_{k'} = 0$ is zeroed out:

$$K(r_k - r_{k'}) = \frac{B}{4\pi|r_k - r_{k'}|^2}; B = \begin{cases} \sum_j \dfrac{4\pi \frac{d_e \sigma_j(\phi_k)}{d\Omega_\phi} N_0^j}{e \sigma_j N_0}, & n = 2. \\ 1, & n > 2 \end{cases} \quad (10)$$

For n=2, the seed photons ($N_{1,\Omega 4\pi}(r_{k'})$ voxel k') are generated by source photons (n=0) primary scattering at voxels k' (n=1). By approximating that the beam is a parallel beam travelling along direction $r_{iso} - r_{source}$, then the angle of Compton-scattering can be determined and incorporated into K (for n=2). For this assumption, the angle-specific Compton-scattering is calculated, spectrum-weighted, normalized, and multiplied by the expected inverse square fall-off with distance (B, n=2). For n>2, the direction of incoming beams is scrambled by the previous kernel treatment, and the kernel simply propagates with the inverse square (B=1). The above processes approximate the exact solution from a MC-like simulation with explicit tracking of each photon's incident and final direction through successive scattering rounds.

The explicit calculation of the attenuation between voxels through the integral term in eq. (9) is not possible with a kernel convolution/superposition. The attenuation is instead approximated with Taylor expansions[21,22] based on the properties of the originating voxels $r_{k'}$, the final voxels $r_k$, and the distance between $r_k - r_{k'}$:

$$\int_{l=r_{k'}}^{l=r_k} \langle \mu(l) \rangle r_{k-k'}^\$ dl \approx \quad (11)$$

$$\langle \exp(-\mu^w | r_k - r_{k'} |)\rangle \left\{ 1 + \left[ 1 - \frac{\rho_e(r_k)}{2} - \frac{\rho_e(r_{k'})}{2} \right] \langle \mu^w \rangle | r_k - r_{k'} | + \right.$$

$$\left. [1 - \rho_e(r_{k'})]^2 \langle (\mu^w)^2 \rangle \frac{|r_k - r_{k'}|^2}{2} \right\}$$

where the largest component (left term) is based on calculating the attenuation as if the material is water with attenuation factor $\mu_j^w$ and corrections are based on the density of the originating and final voxels (the atomic composition is assumed to be the same as water).

A fast Fourier Transform was used to calculate the convolution in eq. (9) after zero-padding to double the length of each dimension (to prevent a circular FT).

The spectrum of the photons generated by eq. (9) is calculated with eq. (7) after replacing $N_0^j \rightarrow N_{n-1,\Omega 4\pi}^{j,norm}$ and $N_{1,\Omega 4\pi}^{j',norm} \rightarrow N_{n,\Omega 4\pi}^{j',norm}$. Thus, each n−1 photon of energy bin j is scattered into a spectrum of energy bin j' photons with amplitudes given by the angle-dependent differential Compton cross-section.

Finally, under an isotropic approximation, for scattering round n, the number of photons scattered by voxel k towards the pinhole is proportional to the pinhole-subtended solid angle divided by $4\pi$:

$$N_{n,\Omega pin}(r_k) = N_{n,\Omega 4\pi}(r_k) \cdot \Omega_k^{pin}/4\pi. \quad (12)$$

The process of kernel propagation and scattering (eqs. (9)-(11)) was repeated for n=2, 3 . . . 6.

Method: Signal Photon Collection

After the above calculations, the total number of photons scattered towards the pinhole by voxel k with energy in bin j' is given by:

$$N_{\Omega pin}^{j'}(r_k) = N_{1,\Omega pin}^{j'}(r_k) + \sum_{n=2}^{6} N_{n,\Omega pin}(r_k) N_{n,\Omega 4\pi}^{j',norm} \quad (13)$$

To attenuate and collect these photons, a new set of rays i' was generated that pass from the center of each imaging pixel (also identified by i') through $r_{pin}$ and into the CT volume. The number of photons per voxel was converted into a photon density, $\rho_{\Omega pin}^{j'}(r_k) = N_{\Omega pin}^{j'}(r_k)/V_{vox}$ and interpolated onto spherical coordinates with grid points defined along the rays i'. Rather than use the rectangular voxel indices k or k', the spherical coordinate voxels are identified by their defining, intersecting ray i' and their distance from the pinhole, indicated with index m. Each ray i' passes through the center of M spherical coordinate voxels, where voxel i',m=M is furthest from $r_{pin}$ and voxel i',m=1 is closest. The distance between successive voxels along any ray i' is chosen to be constant, and, by definition, is also the interaction length ray i' with the spherical coordinate voxel i',m: $l = |r_{i',m} - r_{i',m\pm 1}|$. With this spherical interpolation, the number of photons of energy bin j' reaching each imaging pixel can now be calculated by summing and attenuating along each collection ray:

$$N_{i'}^{j'} = \sum_{m=1}^{M} \rho_{\Omega pin}^{j'}(r_{i',m}) \cdot V_{vox}^m \exp\left[ \sum_{m'=1}^{m-1} -\mu_{j'}(r_{i',m'}) l \right]. \quad (14)$$

Here, the photon density is converted to number of photons by multiplying by the spherical coordinate voxel volume. The exponential attenuation between the scattering voxel and the pinhole is summed over the interceding distance and material. Finally, to approximate the blurring caused by the pinhole, the image was convolved with a binary, 5 mm diameter circular step function.

Method: Validation by Monte Carlo

To validate the analytical model, MC simulations were performed using the same geometries and phantoms as used for the analytical simulations. MC simulations were performed with MC n-Particle v6.0 (MCNP)[23]. An ideal pinhole collimator was simulated by turning off all photon transport in a plane above the phantom except through the pinhole. A FIR tally was used to collect the scatter image. For the FIR tally, each particle collision creates a set of deterministic photon psuedoparticles directed at each FIR pixel. These psuedoparticles are weighted based on the probability that the collision generates photons directed into the solid angle of the FIR pixel. The psuedoparticles undergo attenuation through the material between collision and pixel. Thus, although the interactions and particle transport are based on MC simulation, the image is formed based on psuedoparticles. This FIR tally technique is a method for generating images of scarce events. In the course of the MCNP simulations, <100 true particles were scattered into the pinhole while the FIR psuedoparticles created converged images, as determined by <5% associated standard deviation errors. Coherent scattering was turned off in the MCNP simulations to prevent non-physical signal spiking in the FIR tally images.

Method: Material Properties—$\mu$, $\rho$, Z/A

The material type of each CT voxel was assigned based on the Hounsfield Unit (HU): air (HU<−940), lung (−940≤HU<−200), water (−200≤HU<120), or bone (HU≥120). The density of each CT voxel, $\rho$, was mapped based on the HU using the clinically calibrated relationship for the specific CT scanner.

For the MCNP simulations, each voxel was assigned a density and an atomic mass composition according to the PNNL compendium[24] based on its material type.

For the analytical simulations, from the material type, the Z/A (atomic number/atomic mass) and energy-dependent mass attenuation coefficient $\mu(h\nu)/\rho$ associated with each voxel were drawn from NIST[25]. Air was replaced with vacuum. $\mu(h\nu)/\rho$ was linearly interpolated (on log-log scales) to give the value for energy bin j, $\mu_j/\rho$. The relative electron density was calculated as $\rho_e=(Z/A)\rho/\rho_w$. The attenuation coefficient was calculated as $\mu_j=\rho\cdot\mu_j/\rho$.

Method: Phantoms

Figure 11:
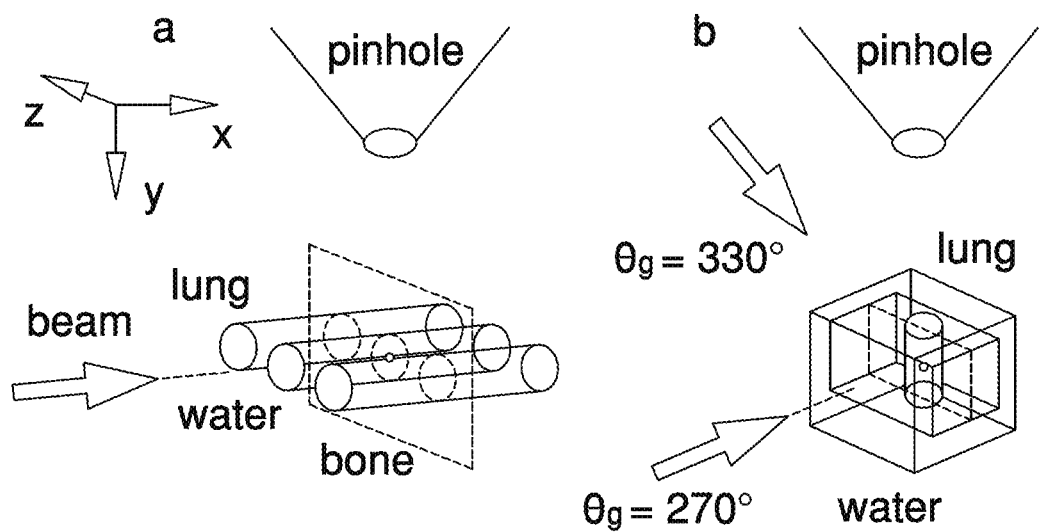
FIG. 11 illustrates several phantom setups.
Figure 11:
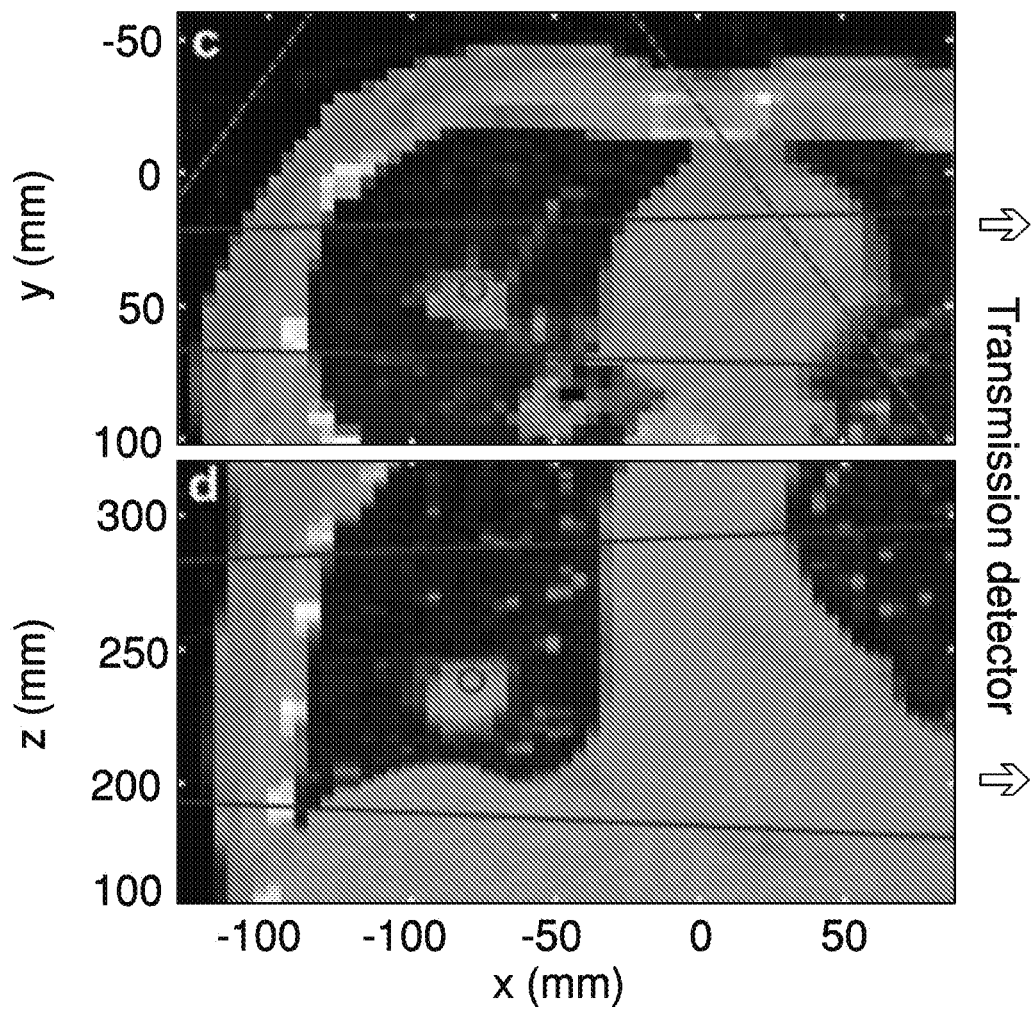

The scatter images resulting from irradiating three different phantoms were simulated: the three cylinder phantom (3C) irradiated with a 15×15 cm² beam ($L_{x/y}\times L_z$), simple lung tumor phantom (LT) irradiated with an 8×8 cm² beam, and lung tumor CT (LTCT) irradiated with a 5×10 cm² beam. The phantoms are shown in FIG. 11. As a simple test case, the 3C phantom is composed of three cylinders of lung, water, and bone. The LT phantom consists of a water cylinder surrounded by lung tissue and an entrance, exit, top, and bottom wall of water. The LTCT was interpolated down to a 4.7×4.6×2 mm³ voxel size to increase the speed of MCNP simulations.

Method: Computers

The MC simulations were performed on a workstation with 16 GB of RAM and a 6 core (2 threads per core) Intel Xeon E5-1660 3.70 GHz CPU. The analytical simulations were performed with 8 GB of RAM and a 4 core Intel Core i7-4770 3.40 GHz CPU.

Results

As shown in FIG. 11, the 3C phantom (a) consists of three 2.8 cm diameter, 7 cm long cylinders ($\rho_{lung}$=0.29, $\rho_{water}$=1.00, $\rho_{bone}$=1.824 g/cm³) with center-to-center spacing of 5.1 cm. The LT phantom (b) is formed by a vertical 2.8 cm diameter water cylinder of 7 cm length centered within a 9×9×11 cm³ lung box. The lung is surrounded on top, bottom, and back by a 2 cm layer of water and 4 cm of water in front (at the $\theta_g$=270° beam entrance). For variable LT source/gantry angles, the phantom and detector are fixed, and the source is rotated around the z axis (eg, the $\theta_g$=330° beam direction is specified). The LTCT phantom axial (c) and coronal (d) slices are shown. The CT is down-sampled to a voxel size of 4.69×4.57×2 mm³. The isocenter is marked with red. The beam direction (a,b) and size (c,d) are marked with purple. The pinhole position (a,b) and field of view (c) are marked with green. For all simulations, the source, pinhole, and detector plane were placed 100, 18.5, and 37 cm, respectively, from isocenter.

Figure 12:
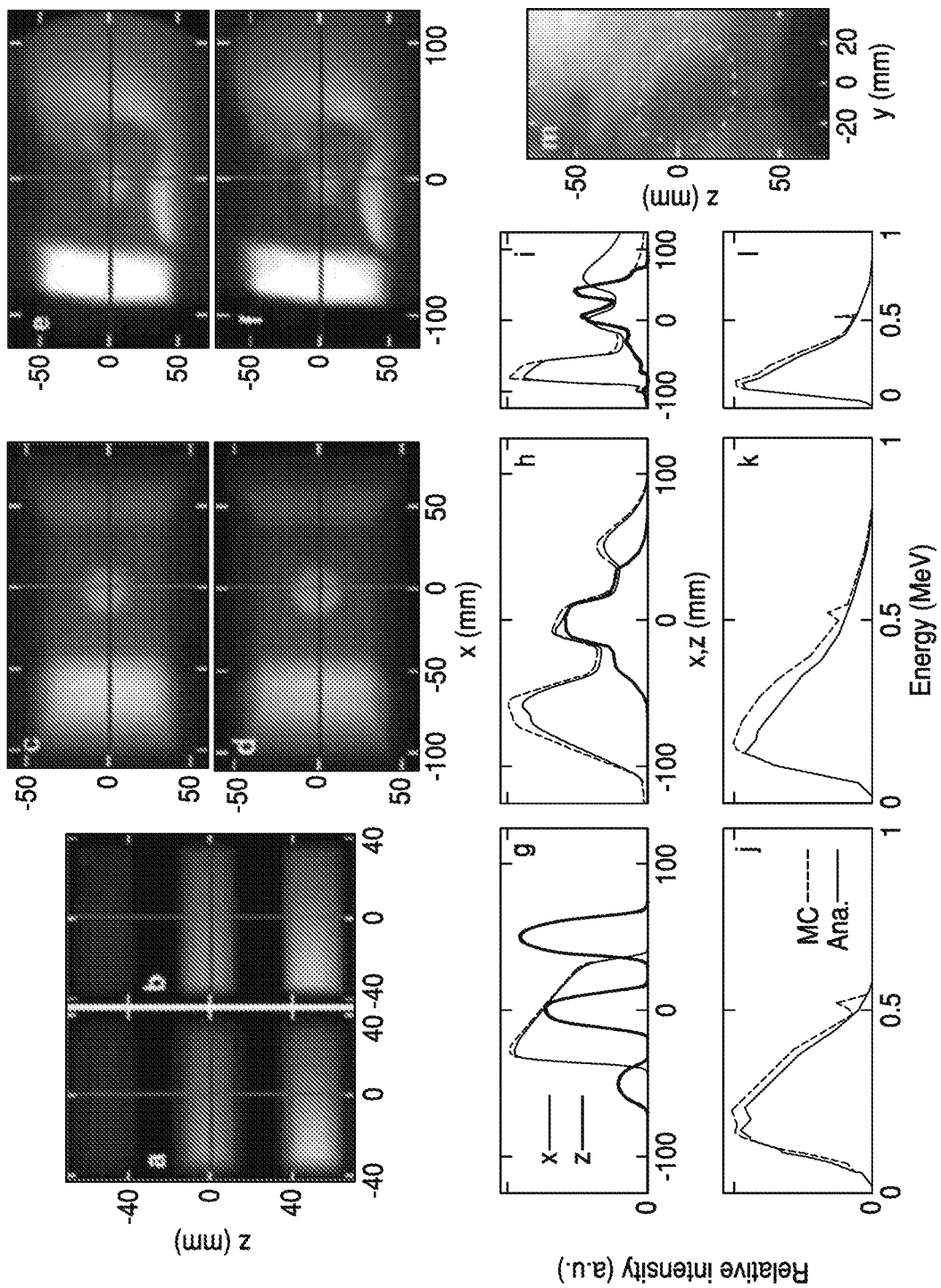
FIG. 12 shows the simulated scatter images for the phantoms.

As shown in FIG. 12, the MCNP (a, c, e) and analytical method (b, d, f) simulated scatter images are shown for the three phantoms: 3C, LT, and LTCT (left to right, respectively). The absolute profiles from each above image (corresponding to the overlaid lines in a-f) along the x and z dimensions are shown in panels g-i. The unnormalized spectra of the above simulated images are shown in j-l. The transmission image (at 50 cm from isocenter) simulated for the LTCT is shown in m with the tumor circled (dashed line).

Figure 13:
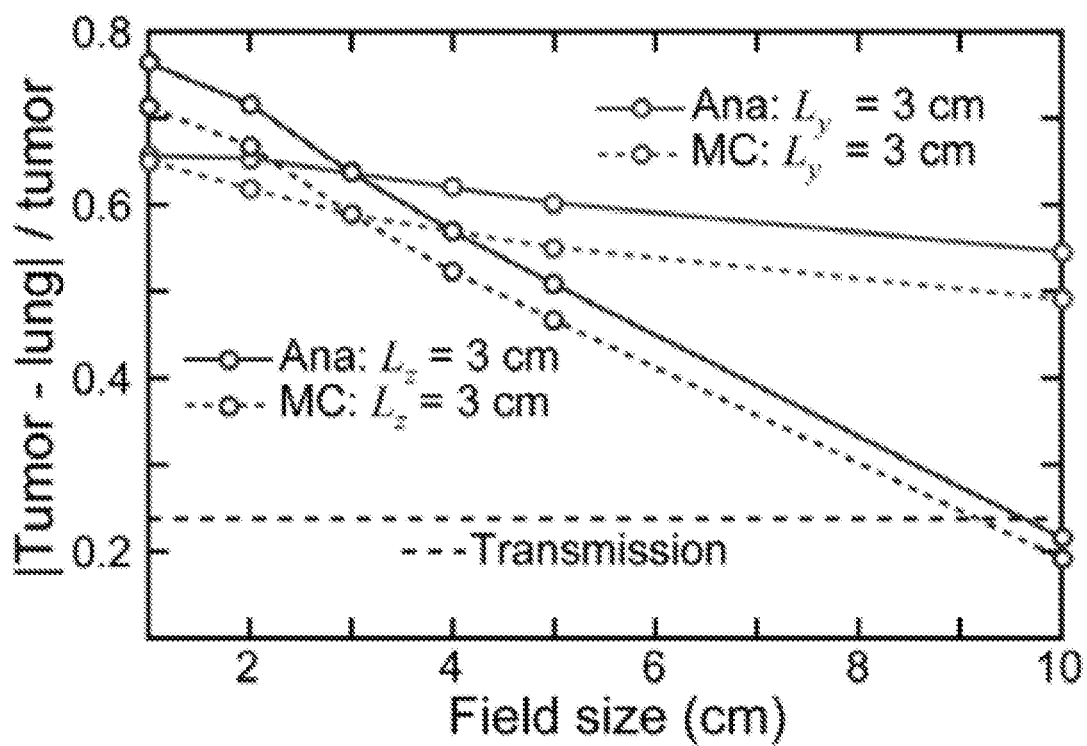
FIG. 13 shows the tumor contrast.

As shown in FIG. 13, the tumor contrast is reported for the LTCT phantom as a function of ant-pos (y axis in FIG. 11 (c)) and sup-inf (z axis in FIG. 11 (d)) beam field size. The contrast for the MV transmission image (FIG. 12 (m)) is also plotted for comparison.

A comparison of the MCNP and analytically simulated scatter images (I) is shown for all three phantoms in FIG. 12. Line profiles show that all features observed in the MCNP images are reproduced in the analytically simulated images. Quantitative pixel-by-pixel comparison shows that, for the pixels in the MCNP images with greater than 10% of the maximum value ($I_{MC}/\max(I_{MC})$>10%), ($I_{ana}-I_{MC}$)/max ($I_{MC}$) has a standard deviation and maximum of 3.1 and 12% for the 3C phantom, 2.9 and 15% for the LT phantom, and 2.4 and 11% for the LTCT. The largest discrepancies between $I_{ana}$ and $I_{MC}$ are at the beam entrance (left side of image), where the analytical simulations under-predict the image intensity by up to 15% relative to the MCNP.

The 3C, LT, and LTCT MCNP-simulated images shown in FIG. 12 required 7.3, 17.9, and 287.5 hours, respectively, to simulate statistically acceptable images (relative error≤0.05 for 1.7×1.7 mm² pixels with image intensity≥10% of the maximum) on two threads of the MCNP computer used here. The corresponding analytically-simulated images required 0.45, 0.39, and 0.27 hours of calculation in MATLAB on the personal computer used here.

For the 3C case, despite the higher attenuation of incident and scattered photons, the densest cylinder (bone) generates the highest intensity image compared to water and lung. Integrating a 19×19 mm² square at the center of each cylinder image gives normalized intensity of 0.28, 1.00, 1.25 for the lung, water, and bone in $I_{ana}$ compared to 0.3, 0.99, 1.29 in $I_{MC}$. Relative to water, the electron densities of lung and bone are 0.29 and 1.71. The tumor in both the LT phantom and LTCT are clearly visible in the scattered images. The image intensity decreases from left to right (along the beam direction) in all three phantom images. The MCNP and analytically simulated spectra agree, although the LT phantom and LTCT analytical spectra are lower at higher energies compared to the MCNP. Negligible intensity is observed above 780 keV. The spectra are peaked at 140-220 keV. Assuming all the photons entering the pinhole come from a point at $r_{iso}$ (i.e. the pinhole is far from the phantom), the integrated intensity of each $I_{MC}$ and $I_{ana}$ is 0.437 and 0.401 (3C), 1.79 and 1.52 (LT), and 1.82 and 1.68 (LTCT) photons per steradian per (source photons per cm²) at $r_{iso}$. For example, from the 3C analytical results, if there is 1 source photon in the 15×15 cm² beam and the 0.25 cm radius pinhole is 18.5 cm from $r_{iso}$, then 0.401 sr⁻¹ cm²×$\pi$ $(0.25)^2/18.5^2$ sr×1 photon/(15×15) cm⁻²=1.0×10⁻⁶ photons are scattered into the pinhole.

The tumor contrast relative to the surrounding lung was calculated for the LTCT phantom simulated scatter images and plotted in FIG. 13. The contrast is calculated as |$\bar{I}_{tumor}-\bar{I}_{lung}$|/$\bar{I}_{tumor}$, where $\bar{I}$ is the average intensity in an area assigned to either the tumor or the surrounding lung. As the sup-inf field size ($L_z$, perpendicular to the pinhole axis) is increased from 1 to 10 cm, there is a small drop in the contrast (by 0.16 and 0.10 for the MC and analytical images, respectively). A much larger drop in contrast (by 0.52 and 0.55, MC and analytical) is observed for increasing ant-post field size ($L_y$, along the pinhole axis). Of the simulated field sizes, the highest contrast (0.71, MC; 0.76 analytical) is observed in the 1×3 cm² ($L_y$×$L_z$) case. The analytical simulations similarly demonstrate the field-size dependent contrast effects. The tumor-lung contrast in the MV transmission image (FIG. 12 (m)) is 0.24.

Figure 14:
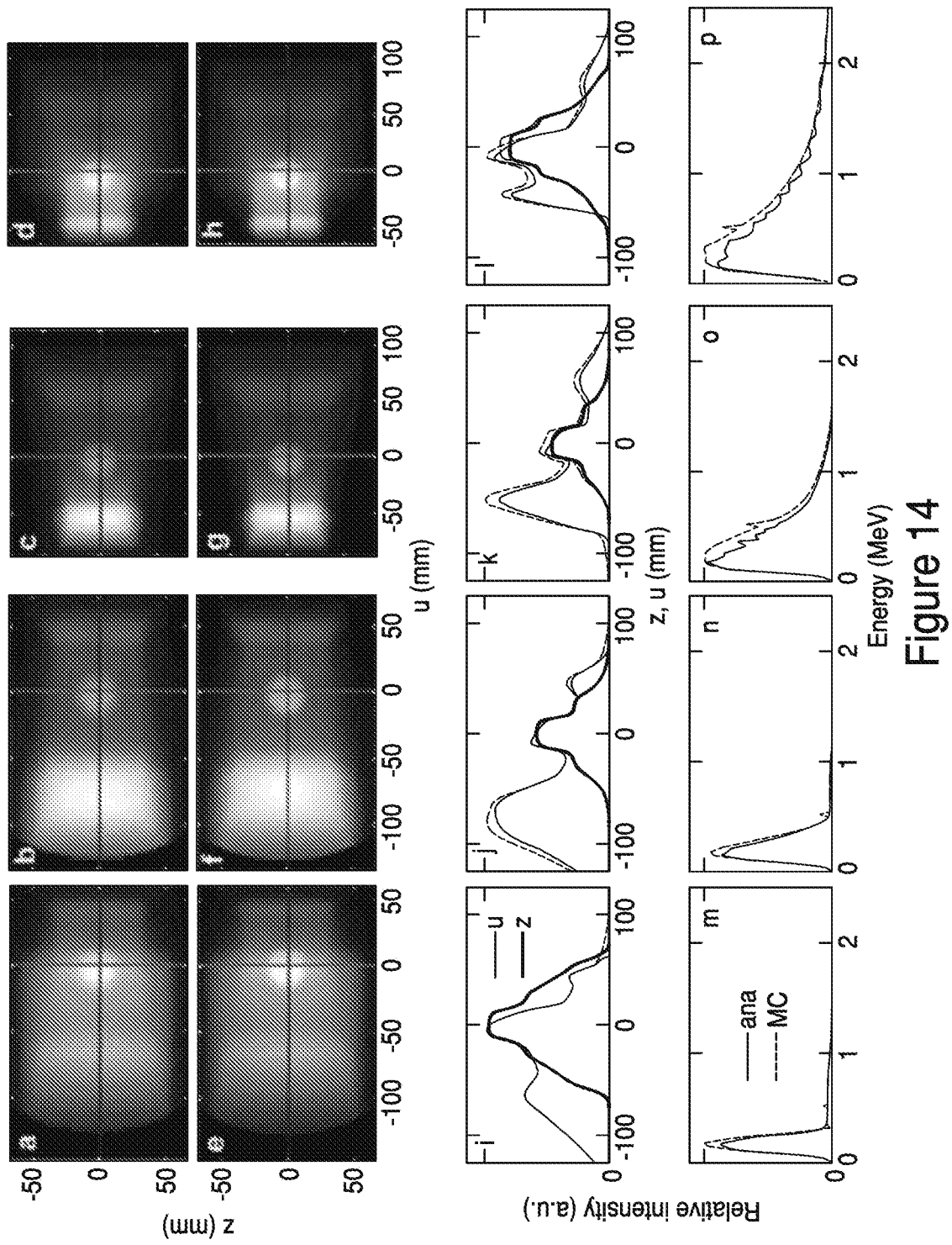
FIG. 14 shows simulated scatter images of one phantom irradiated at different source angles.

The LT phantom images simulated for gantry angles of $\theta_g$=330, 300, 240, and 210° (source-isocenter-pinhole angles of 30, 60, 120, and 150°) are shown in FIG. 14. As with the $\theta_g$=270° case (FIG. 12), the line profiles show good agreement between $I_{ana}$ and $I_{MC}$. There is a complicated relationship between source-isocenter-pinhole angle and number of photons that reach the pinhole. Compared to the $\theta_g$=270° case (FIG. 12), the integrated $I_{ana}$ intensity for the other four angles considered here is 2.38, 1.97, 2.19, and 4.53 photons per steradian per (source photons per cm²). As the source-isocenter-pinhole angle increases, the mean energy of the spectrum increases.

As shown in FIG. 14, the MCNP (a-d) and analytically (e-h) simulated scatter images are shown for the LT phantom irradiated at different source angles: from left to right $\theta_g$=330, 300, 240, 210°. The absolute profiles from each above image (corresponding to the overlaid lines in a-h) along the x and z dimensions are shown in panels i-l. The unnormalized spectra of the above simulated images are shown in m-p.

Figure 15:
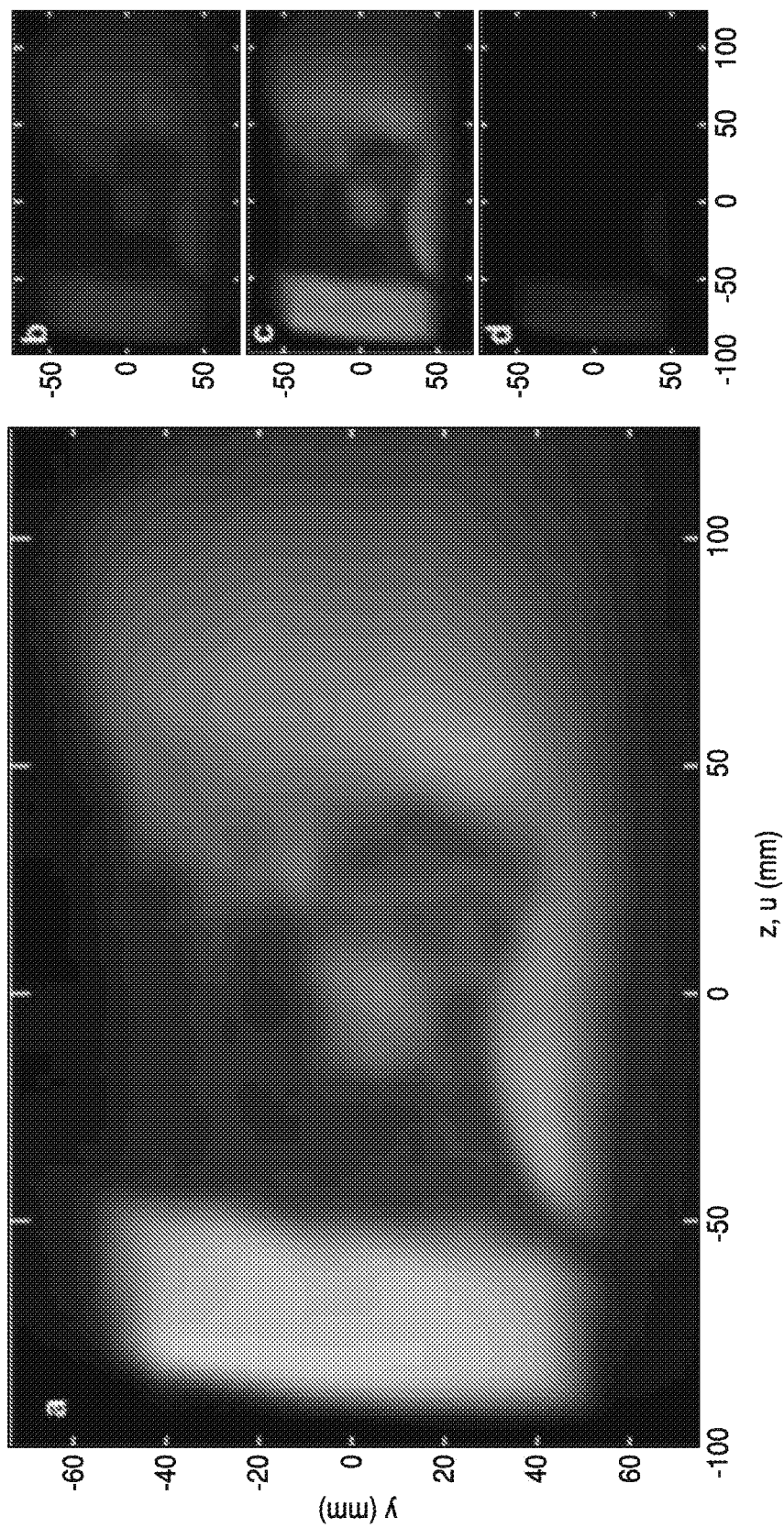
FIG. 15 shows a false-color, energy-resolved image of one phantom.

As shown in FIG. 15, a false-color, energy-resolved image of the LTCT analytically simulated scatter image is shown in a. The component images (b-d) are formed by summing energy-resolved images over the 0-190, 190-325, and >325 keV energy ranges, respectively.

Figure 16:
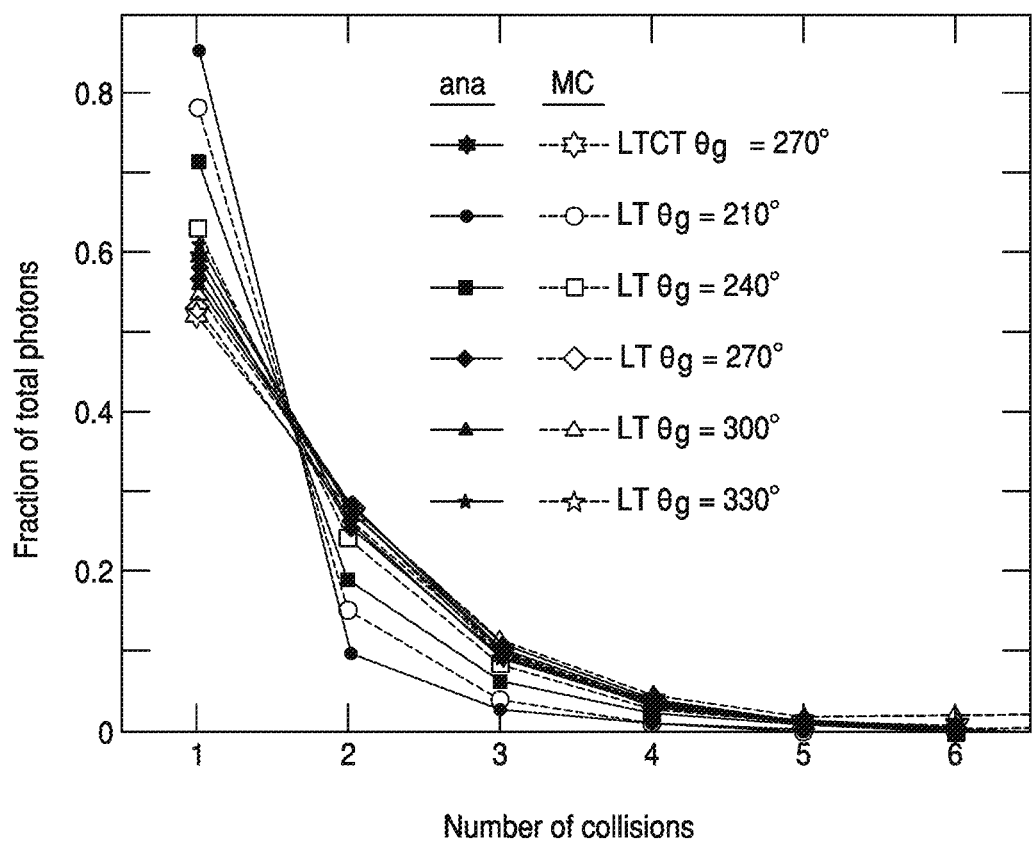
FIG. 16 shows the fraction of photons that pass through the pinhole after 1-6 collisions for different phantoms and source beam angles.

As shown in FIG. 16, the fraction of photons that pass through the pinhole after 1-6 collisions is plotted for different phantoms and source beam angles. The MC and analytically simulated results are shown.

Figure 17:
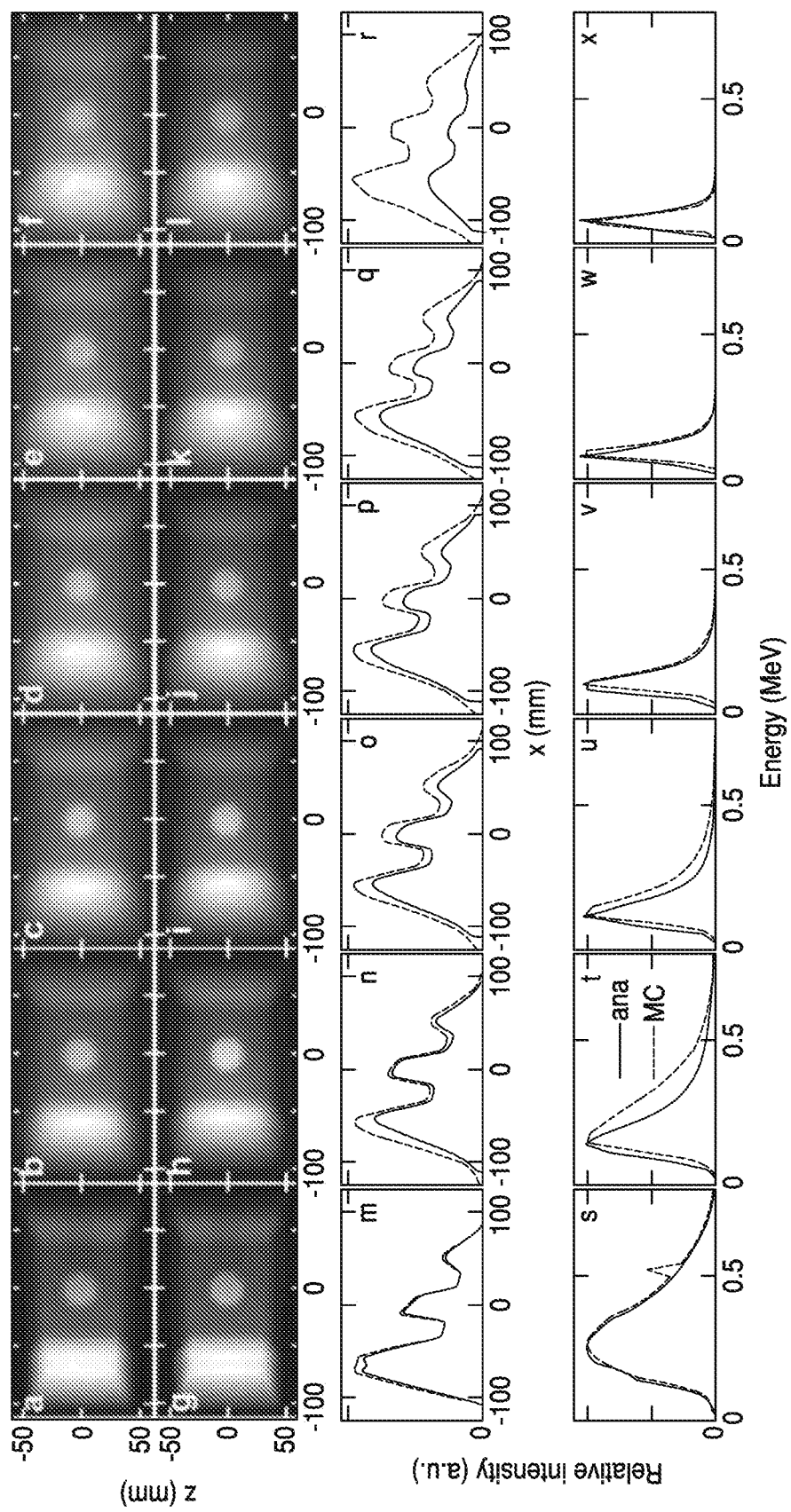
FIG. 17 shows the collision-number separated scatter images.

As shown in FIG. 17, the collision-number separated MCNP (a-f) and analytically (g-l) simulated LT phantom ($\theta_g$=270°) scatter images are shown. From left-to-right, the images formed by n=1, 2, 3, 4, 5 and 6 order—scattered photons are shown. The MCNP image f is formed for collisions 6≤n<100, which may explain the profile amplitude discrepancy in r. The absolute profiles from each above image along the x dimensions (z=0.85 mm) are shown in panels m-r. The normalized spectra of the above simulated images are shown in s-x.

A false color analytically simulated scatter image is shown in FIG. 7. After binning the photon energies into three ranges, the intensity of each scattered photon energy bin is visualized with three colors. As the source-voxel-pinhole angle decreases, Compton-scattering angle ($\phi_{i,k}^{pin}$) increases and scattered photon energy decreases. Thus, the photons from the front face of the LTCT have the highest energy, while those at the back have the lowest. Low energy photons appear at the top and bottom edge of the image, beyond the irradiating field boundaries due to multiple-scatter.

The number of photons that reach the pinhole as a result of $n^{th}$ order scattering are shown in FIG. 16 for both the LT and LTCT cases (for $\theta_g$=270°). The ratios of analytically-simulated photons match those from MCNP. In both phantoms, 50-60% of photons that reach the pinhole are primary-scattered. The ratio then drops off exponentially, and the $5^{th}$ order scattering only contributes≤2%. For obtuse (120° and 150°) source-isocenter-pinhole angles ($\theta_g$=240° and 210°), the $1^{st}$ order scattering contributes a larger fraction (up to 80%) of the total photons that enter the pinhole. Because the n=1 and 2 collisions generate 80-96% of the imaged photons in all the considered cases, the lines connecting n=1 and n=2 data points cross n~1.5 between 0.4 and 0.48.

FIG. 17 plots the images, line profiles, and spectra associated with each $n^{th}$ order scattering round simulated for irradiation of the LT phantom. Qualitatively, increasing the scattering order blurs the image and causes a more homogeneous distribution of intensity. The primary images $I_{ana}^{n=1}$ and $I_{MC}^{n=1}$ match well, as do their spectra. The entrance intensity discrepancy ($I_{MC}>I_{ana}$ on the left side of the image) results from differences in the higher order scattering images ($I_{ana}^{n>1}$). The 1<n≤3 analytical spectra have lower intensity than the MCNP spectra above 150 keV. The 511 keV positron-annihilation peak is present in the n=1 MCNP spectrum, but not in the analytically-simulated nor higher-order MCNP spectra. Pair production was not included in the analytically simulated method because its contribution is <1% of the total collected photons. If desired, inclusion of pair production is straightforward: photons incident at each voxel are converted to 511 keV emitted photons based on the known pair production cross sections.

Discussion

Primary scatter photons are generated when the therapeutic beam interacts with matter. Therefore, scatter images may be obtained and used to determine which structures have been irradiated. For each of the shown images, the radiation source is to the left, the imaging pinhole is placed at 90° perpendicular to the beam axis (unless otherwise noted, as in FIG. 14), and the portal transmission image is collected to the right. As shown in the presented simulated images, scatter imaging has the potential to provide high contrast images collected at arbitrary angles relative to the treatment beam. For example, FIGS. 4+7 shows the scatter image simulated from a CT phantom. From the detector's position, an orthogonal image of the irradiated structures may be obtained. The image intensity is higher on the left side of the images because the irradiating beam is attenuated from left-to-right as it penetrates the phantoms.

The scatter images simulated with the presented analytical method closely match those simulated with MC. The MC and analytical method primary scatter images and spectra match well, as is expected given the similarity in how they are calculated. In the MC case, the primary scatter image is generated by deterministic psudeoparticles after collisions in the phantom. In the analytical method, the percentage of photons scattered is calculated analytically, and incident and outgoing attenuation is calculated through ray-tracing. Differences in the primary images can be attributed to pinhole blurring—MCNP uses ray tracing through an explicit pinhole while the analytical technique relies on post-processing convolution of the ideal image with a pinhole function—and the discretized nature of both the source and scattered spectra used in the analytical method; the analytical method uses a finite set of photon energies, while the MC simulation allows for a complete sampling (compared in FIG. 10). This discretization is also the cause of the jagged spectrum analytically simulated for the $\theta_g$=240 and 210° (FIG. 14; see the unnormalized spectra shown in o and p).

The discrepancy between MC and analytically simulated images is largely due to approximations in the convolution/superposition technique used for higher-order scattering in the analytical method. For the convolution/superposition technique there are two major assumptions. The first is that the attenuation between successive scattering events is approximated by the Taylor expansion given in eq. (11): the material between voxels is first assumed to be water, and then corrections are made based on the density of the originating voxel ($r_{k'}$) and the scattering voxel ($r_k$) and the distance between. The $r_{k'}$ and $r_k$ material corrections assume that the voxels have the same atomic composition (and therefore μ/ρ attenuation curve) as water, which is valid for lung and bone above 100 keV. Based on the approximations, the biggest errors are expected in highly heterogeneous materials and near interfaces[21]. From FIG. 12 (e), (f), (i), the analytical technique appears to faithfully reproduce features and intensities despite the heterogeneous nature of the lung tissue. The lung tissue scatter intensity is under-predicted by the analytical technique, which may be a result of the approximation.

The analytical technique convolution/superposition method also assumes that the scattered photons are scattered isotropically. But, the scattering probability and energy of scattered photon are both scattering-angle dependent (eqs. (2) and (3)). The manifestation of this isotropic approximation is that the analytical spectrum intensity for the n=2 and 3 order scattering is too low at high energies (hv'>150 MeV). The isotropic approximation become more valid at higher scattering order, and the spectrum discrepancy is not observed for n≥4.

For the three phantoms investigated here and using similar computer processors, the analytical simulation is up to 1000 times faster to compute than the MC simulation. This speed advantage increases with the complexity and resolution of the phantom because the MCNP simulation time is highly dependent on these factors while the analytical simulation time is not. The analytical simulations were completed in ~30 minutes in MATLAB without the parallelization toolbox. Almost all of the computations in the analytical simulation method are parallelizable (ray-tracing, FFT), which suggests that the algorithm might be re-written using a faster coding language and implemented on a parallelized GPU cluster to achieve sub-minute (possibly sub-second) computational times.

The presented images show the potential of scattering imaging, which provides high contrast images of the irradiated materials. The position of the detector is only constrained to regions outside of the beam path. Unlike portal transmission imaging, which only gives a beam's eye view of the cumulative attenuation experienced by the beam over its entire pathlength, scatter imaging can provide multiple simultaneous views of the irradiated volume. As shown in FIGS. 4+7, the scatter images may be collected at multiple views from multiple angles. The LTCT phantom scatter image provides a high contrast image with a discernable lung tumor, a feature that is difficult to identify in the transmission image (FIG. 12 (m). FIG. 13). Because of the orthogonal view provided by the scatter image, the features in the 3C and LT phantoms lost in the null-space of their transmission images (not shown) are discernable in the scatter images.

Because scattered photons only originate from irradiated volumes (with the exception of multiple-order scattering), the imaged volume and resulting contrast depend on the field size, as is shown in FIG. 13. Increasing the field size above and below the tumor (in this case, ant-pos, along the y axis of FIG. 11 (c)) generates increased scattered photons from lung tissue above and below the tumor without additional photons from the tumor, and contrast decreases. Increasing the field size sup-inf (along the z axis, FIG. 11 (d)) is clearly observed in the scatter image—a larger area in the image field-of-view "lights up"—but the tumor-lung contrast is only slightly decreased (due to multiple-scattering photons). Although the focus of this work is to collect images using photons scattered from the therapy beam, use of an external photon source allows for more flexibility in creating ideal irradiation fields for maximizing feature contrast. For example, use of a fan-beam irradiation allows for selective scatter imaging of a slice of a patient[13], resulting in an image analogous to a CT slice. The higher contrast (0.71) observed in the scatter images compared to transmission images (0.24, FIG. 13) has been predicted[26] and shown in simulation[13,14] and experiment previously, which suggests that scatter imaging may be advantageous compared to transmission imaging.

Because it is generated by scattering of the beam, scatter images may potentially be used for tumor tracking. For example, if the lung tumor in FIG. 12 (e)+(f) leaves the beam (due to breathing motion, for example), than it will not appear on the image. Along with portal transmission imaging, kV imaging is currently used for tumor tracking. kV imaging delivers extra dose to the patient, its view is constrained either by its ceiling/floor mounting or at 90° relative to the beam, as in the case of on-board imaging. kV imaging is also a transmission technique that lacks the contrast of scatter imaging, where only irradiated features appear in the image. If the tumor leaves the treatment field, kV imaging relies on accurate radiation/imaging coordinate registration to identify the issue.

The results presented here not only show what scatter images will look like, but they also indicate the expected energy and number of scattered photons. When placed at 90° relative to the 6 MV FFF beam, the detected scatter energy spectrum peaks at 140-220 keV, drops abruptly at lower energies, and trails off more gradually to 700-800 keV. When the detector is placed at an acute angle relative to the beam, the scattered photons are of lower energy, up to 350 keV (FIG. 14 (m)+(n)). For obtuse source-isocenter-pinhole angles, the scattered photons are of higher energy, up to >2 MeV (FIG. 14 (o)+(p)). The scatter images also exhibit spatial energy-dependence, as shown in FIG. 15. When the source-voxel-pinhole angle is larger, the Compton-scattering angle is smaller, and higher energy photons are scattered into the pinhole. No portion of the image is monoenergetic, however, due to the polyenergetic source spectrum and the importance of multiple scattering events.

For the 6 MV FFF beam considered here, 10 cGy of dose is calculated by MCNP to be deposited in water at $d_{max}$ by $1.95 \times 10^{10}$ photons/cm$^2$ (10×10 cm$^2$ field, central axis, 100 cm SSD). For the LT phantom with the pinhole placed 90° relative to the beam at 18.5 cm from isocenter, the simulations predict that $1.7 \times 10^7$ photons will pass through the 5 mm diameter pinhole to deliver an average $1 \times 10^3$ photons per mm$^2$ at the imaging plane (1:1 magnification ratio from isocenter to imaging plane). For the same collimator geometry and deposited dose, an average of $6 \times 10^2$ photons are expected per mm$^2$ for the LTCT phantom.

Of the photons that contribute to the scatter image, 40-50% are from multiple scattered photons (FIG. 16), although increasing the source-isocenter-pinhole angle above 90° decreases the contribution. The multiple scattering redistributes initially scattered photons throughout the phantom. Although the multiple scattering is also linear in the electron density, the n>1 scatter images appear blurred because the photons incident at each voxel no longer originate from a known source ($r_{source}$). For primary scattered photons, there are clear origin boundaries as defined by the therapy field edges. For higher-order scattering, photons leak out of the field volume (the low energy blurring at the top and bottom of FIG. 15 (a)). Two possible applications of scattering imaging—volumetrically measuring the phantom electron density and spatially quantifying deposited dose—are detrimentally affected by the blurring caused by multiple scattering because the intensity of scatter from a voxel of interest also depends on the surrounding voxels. To improve the accuracy of electron density determination, many attempts have been made to reduce the contribution from multiple scattering by localizing the scattering volume with a narrow beam and focused collimator[1,27], energy-discrimination[2,11,18], and/or collecting at reduced scattering angles[20]. Despite these advances, multiple scattering and attenuation have limited electron density determination to a 4.3% standard deviation (for 0.11 Gy of delivered dose)[12]. Quantification of deposited dose based on scatter image intensity has not been tested, possibly because it is also complicated by the multiple-scattering blurring. Energy-discriminating gamma cameras may be able to perform a statistical determination, although processing may take days of computation[7]. The analytical simulation method described here may provide a faster iterative route through which agreement of experimental and simulated images would allow for 3D quantification of deposited dose.

The analytical simulation method described here assumes an ideal pinhole collimator (no septal nor collimator penetration) and an ideal, noiseless detector that collects all incident photons. In reality, a finite thickness collimator is expected to transmit some of the high energy photons. Collimator penetration is expected to cause a broad, inverse-squared background in the image. Septal penetration is expected to blur the image and cause a decrease in spatial resolution. The energy-response of the detector will cause a low-energy weighting of the image. The full manifestation of these realistic effects is unknown, but preliminary experimental images suggest that quality images are achievable with low dose deposition[14]. Despite the current absence of these processes in the described analytical simulation technique, the method provides a fast and accurate algorithm for generating the ideal image. From the ideal image, the potential information content, expected photon energies, and underlying physics can be assessed. Therefore, we consider the described technique as a necessary step for fully characterizing scatter imaging.

Although it is used here for scatter imaging, the analytical simulation technique may possibly be applied more generally to model Compton-scattering within complex phantoms regardless of the origin of the source photons, such as for SPECT, PET, and proton prompt gamma imaging[15,16].

Conclusion

Compton-scattered photons carry information about the irradiated volume. By localizing the origin of these photons with a pinhole collimator, images may be formed that reveal the treatment beam path through the patient anatomy. Unlike other forms of tumor-tracking imaging. Compton-scatter imaging does not require additional ionizing radiation (compare to on-board imaging) and simultaneous images may be collected from multiple angles and positions (compare to portal imaging). Here, a computationally fast—up to 1000× faster than MC—analytical method for simulating scatter images is described and validated with three phantoms through comparison to MC. Based on the simulations, placing a pinhole collimator orthogonal to the 6 MV FFF treatment beam will result in collection of <780 keV photons with a spectrum that peaks at 140-220 keV. Of these photons, 40-50% are due to multiple order scattering. For the considered phantoms and pinhole, depositing 10 cGy at $d_{max}$ is expected to generate an average $1\times10^3$ photons per $mm^2$ at the (unmagnified) detector plane. The analytical method described here may serve to generate simulated images for real-time comparison to experimental scatter images for the purpose of tumor tracking. The method may also find application to other imaging techniques where modeling Compton-scattering is important.

References

1. P. G. Lale, "The Examination of Internal Tissues, using Gamma-ray Scatter with a Possible Extension to Megavoltage Radiography," Physics in Medicine and Biology 4, 159 (1959).
2. F. T. Farmer and M. P. Collins, "A new approach to the determination of anatomical cross-sections of the body by Compton scattering of gamma-rays," Phys Med Biol 16, 577-586 (1971).
3. R. L. Clarke, E. N. Milne and G. Van Dyk, "The use of Compton scattered gamma rays for tomography," Investigative radiology 11, 225-235 (1976).
4. G. Harding and R. Tischler, "Dual-energy Compton scatter tomography," Physics in Medicine and Biology 31, 477 (1986).
5. S. J. Norton, "Compton scattering tomography," Journal of Applied Physics 76, 2007-2015 (1994).
6. M. Lenti, "A 3-D imaging device using Compton scattering off the body," Nuclear Instruments and Methods in Physics Research Section A: Accelerators, Spectrometers, Detectors and Associated Equipment 588, 457-462 (2008).
7. D. W. Mundy and M. G. Herman, "Uncertainty analysis of a Compton camera imaging system for radiation therapy dose reconstruction," Medical physics 37, 2341-2350 (2010).
8. K. P. MacCabe, A. D. Holmgren, M. P. Tornai and D. J. Brady, "Snapshot 2D tomography via coded aperture x-ray scatter imaging," Appl. Opt. 52, 4582-4589 (2013).
9. E. Odeblad and Å. Norhagen, "Measurements of Electron Densities with the Aid of the Compton Scattering Process," Acta Radiologica os-45, 161-167 (1956).
10. R. L. Clarke and G. Van Dyk, "A new method for measurement of bone mineral content using both transmitted and scattered beams of gamma-rays," Phys Med Biol 18, 532-539 (1973).
11. J. J. Battista, L. W. Santon and M. J. Bronskill, "Compton scatter imaging of transverse sections: corrections for multiple scatter and attenuation," Phys Med Biol 22, 229-244 (1977).
12. J. J. Battista and M. J. Bronskill, "Compton scatter imaging of transverse sections: an overall appraisal and evaluation for radiotherapy planning," Phys Med Biol 26, 81-99 (1981).
13. H. Yan, Z. Tian, Y. Shao, S. B. Jiang and X. Jia, "A new scheme for real-time high-contrast imaging in lung cancer radiotherapy: a proof-of-concept study," Phys Med Biol 61, 2372-2388 (2016).
14. G. Redler, D. Bernard, A. Templeton, C. Kumaran Nair, J. Turian and J. Chu, "MO-AB-BRA-2: A Novel Scatter Imaging Modality for Real-Time Image Guidance During Lung SBRT," in *AAPM 57th Annual Meeting and Exhibition*, (Anaheim, CA, 2015).
15. H. Zaidi and K. F. Koral, "Scatter modelling and compensation in emission tomography," European journal of nuclear medicine and molecular imaging 31, 761-782 (2004).
16. B. F. Hutton, I. Buvat and F. J. Beekman, "Review and current status of SPECT scatter correction," Phys Med Biol 56, R85-112 (2011).

17. R. L. Siddon, "Fast calculation of the exact radiological path for a three-dimensional CT array," Medical physics 12, 252-255 (1985).
18. R. L. Clarke and G. Van Dyk, "COMPTON-SCATTERED GAMMA RAYS IN DIAGNOSTIC RADIOGRAPHY," Medical Radioisotope Scintigraphy. Vol. I. Vienna, International Atomic Energy Agency 1, 247-680 (1969).
19. F. T. Farmer and M. P. Collins, "A further appraisal of the Compton scattering method for determining anatomical cross-sections of the body," Phys Med Biol 19, 808-818 (1974).
20. J. J. Battista and M. J. Bronskill, "Compton-scatter tissue densitometry: calculation of single and multiple scatter photon fluences," Phys Med Biol 23, 1-23 (1978).
21. A. L. Boyer and E. C. Mok, "Calculation of photon dose distributions in an inhomogeneous medium using convolutions," Medical physics 13, 503-509 (1986).
22. E. Wong, Y. Zhu and J. Van Dyk, "Theoretical developments on fast Fourier transform convolution dose calculations in inhomogeneous media," Medical physics 23, 1511-1521 (1996).
23. T. Goorley, M. James, T. Booth, F. Brown, J. Bull, L. J. Cox, J. Durkee, J. Elson, M. Fensin, R. A. Forster, J. Hendricks, H. G. Hughes, R. Johns, B. Kiedrowski, R. Martz, S. Mashnik, G. McKinney, D. Pelowitz, R. Prael, J. Sweezy, L. Waters, T. Wilcox and T. Zukaitis, "Initial MCNP6 Release Overview," Nuclear Technology 180, 298-315 (2012).
24. R. McConn Jr., C. Gesh, R. Pagh, R. Rucker and R. Williams III, "Compendium of Material Composition Data for Radiation Transport Modeling," PNNL-15870 Rev. 1 (2011).
25. J. H. Hubbell and S. M. Seltzer, "Tables of X-Ray Mass Attenuation Coefficients and Mass Energy-Absorption Coefficients from 1 keV to 20 MeV for Elements Z=1 to 92 and 48 Additional Substances of Dosimetric Interest," in NISTIR 5632, (1996).
26. G. Harding, "Inelastic photon scattering: Effects and applications in biomedical science and industry," Radiation Physics and Chemistry 50, 91-111 (1997).
27. P. G. Lale, "The Examination of Internal Tissues by High-Energy Scattered X Radiation," Radiology 90, 510-517 (1968).

While the particular invention has been described with reference to illustrative embodiments, this description is not meant to be limiting. Various modifications of the illustrative embodiments and additional embodiments of the invention will be apparent to one of ordinary skill in the art from this description. Those skilled in the art will readily recognize that these and various other modifications can be made to the exemplary embodiments, illustrated and described herein, without departing from the spirit and scope of the present invention. It is therefore contemplated that the appended claims will cover any such modifications and alternate embodiments. Certain proportions within the illustrations may be exaggerated, while other proportions may be minimized. Accordingly, the disclosure and the figures are to be regarded as illustrative rather than restrictive.

The invention claimed is:

1. An apparatus for performing real-time energy-resolved scatter imaging during radiation therapy image guidance upon a patient, the apparatus comprising:
a collimator comprising an opening, the collimator configured to allow a portion of scattered radiation from a treatment region irradiated with external x-ray photons in a patient to pass through the opening;
a radiation detector configured to detect the portion of scattered radiation passing through the opening, the radiation detector providing a first signal when photon energy of the detected portion of scattered radiation is within a first energy range between about zero and about 100 keV, the radiation detector providing a second signal when photon energy of the scattered radiation is within a second energy range between about 100 keV and about 325 keV, and the radiation detector providing a third signal when photon energy of the scattered radiation is within a third energy range between about 325 keV and about 24 Mev wherein the first energy range is different from the second energy range and the third energy range, and wherein the second energy range is different from the third energy range; and
an image controller configured to receive the first signal, second signal and the third signal from the radiation detector, wherein:
the image controller is configured to convert the first signal into a first image data set, the second signal into a second image data set, and the third signal into a third image data set,
the image controller is configured to perform an image operation on the first, second, and third image data sets to obtain an energy-resolved scatter image data set,
wherein the radiation detector is configured to determine photon energy of the detected portion of scattered radiation by measuring an amplitude of a detection spike corresponding to a photon in the detected portion of scattered radiation, and
wherein the energy-resolved scatter image data set is provided in real-time thereby guiding radiation therapy upon the patient.

2. The apparatus of claim 1, wherein the radiation detector comprises a first detection layer, a second detection, and a third detection layer.

3. The apparatus of claim 2, wherein:
the detected portion of scattered radiation comprises a first portion, a second portion,
and a third portion, the first portion comprising lower energy photons on average than
the second and third portion;
the first portion is configured to be absorbed and detected by the first detection layer;
the second portion is configured to transmit through the first detection layer and be absorbed and detected by the second detection layer; and
the third portion is configured to transmit through the first and second detection layer and be absorbed and detected by the third detection layer.

4. The apparatus of claim 1, wherein the opening of the collimator has a diameter between about 0.1 cm and about 1 cm.

5. The apparatus of claim 1, wherein:
the opening of the collimator is disposed at a first distance away from the treatment region;
the radiation detector comprising an array of radiation detecting sensors, wherein the array of radiation detecting sensors are disposed at a second distance away from the opening of the collimator; and
a magnification ratio between the second distance and the first distance is between about 0.5 and about 2.

6. The apparatus of claim 1, wherein the image controller is configured to:
assign the first image data set into a first color channel;

assign the second image data set into a second color channel;

assign the third image data set into a third color channel; and combine the first image data set in the first color channel, the second image data set in the second color channel, and the third image data set in the third color channel to obtain the energy-resolved scatter image data set with multiple colors.

7. The apparatus of claim 1, wherein the image controller is configured to:

multiply the first image data set by a first numerical factor to obtain a fourth image data set;

multiply the second image data set by a second numerical factor to obtain a fifth image data set; and subtract the fourth image data set from the fifth image data set to obtain the energy-resolved scatter image data set.

8. The apparatus of claim 1, wherein a scattering angle between a first direction aligned with a radiation beam and a second direction aligned with detected portion of scattered radiation is between about 30° and about 150°.

9. A system for performing real-time energy-resolved scatter imaging during radiation therapy image guidance upon a patient, the system comprising:

a radiation source configured to deliver a radiation beam to a treatment region;

a collimator comprising an opening, the collimator configured to allow a portion of scattered radiation from a treatment region irradiated with external x-ray photons in a patient to pass through the opening;

a radiation detector configured to detect the portion of scattered radiation passing through the opening, the radiation detector providing a first signal when photon energy of the detected portion of scattered radiation is within a first energy range between about zero and about 100 keV and the radiation detector providing a second signal when photon energy of the scattered radiation is within a second energy range between about 100 keV and about 325 keV, and the radiation detector providing a third signal when photon energy of the scattered radiation is within a third energy range between about 325 keV and about 24 Mev wherein the first energy range is different from the second energy range and third energy range, and wherein the second energy range is different from the third energy range; and an image controller configured to receive the first signal, the second signal, and the third signal from the radiation detector, wherein:

the image controller is configured to convert the first signal into a first image data set, the second signal into a second image data set, and the third signal into a third image data set, and the image controller is configured to perform an image operation on the first, second, and third image data sets to obtain an energy-resolved scatter image data set, and wherein the radiation detector is configured to determine photon energy of the detected portion of scattered radiation by measuring an amplitude of a detection spike corresponding to a photon in the detected portion of scattered radiation, wherein the energy-resolved scatter image data set is provided in real-time thereby guiding radiation therapy upon the patient.

10. The system of claim 9, wherein the radiation detector comprises a first detection layer, a second detection layer, and a third detection layer.

11. The system of claim 10, wherein:

the detected portion of scattered radiation comprises a first portion, a second portion, and a third portion, the first portion comprising lower energy photons on average than the second and third portion;

the first portion is configured to be absorbed and detected by the first detection layer; and the second portion is configured to transmit through the first detection layer and be absorbed and detected by the second detection layer; and the third portion is configured to transmit through the first and second detection layer and be absorbed and detected by the third detection layer.

12. The system of claim 9, wherein the image controller is configured to:

assign the first image data set into a first color channel;

assign the second image data set into a second color channel;

assign the third image data set into a third color channel; and combine the first image data set in the first color channel, the second image data set in the second color channel, and the third image data set in the third color channel to obtain the energy-resolved scatter image data set with multiple colors.

13. The system of claim 9, wherein the image controller is configured to:

multiply the first image data set by a first numerical factor to obtain a fourth image data set;

multiply the second image data set by a second numerical factor to obtain a fifth image data set; and subtract the fourth image data set from the fifth image data set to obtain the energy-resolved scatter image data set.

14. A method for performing real-time energy-resolved scatter imaging during radiation therapy image guidance upon a patient, the method comprising:

detecting, by a device comprising a radiation detector, a collimator in front of the radiation detector, and an image controller in communication with the radiation detector, a first signal, a second signal, and a third signal from a portion of scattered radiation from a treatment region in a patient region irradiated with external x-ray photons delivered from a radiation source to the treatment region in the patient, the first signal having a first photon energy in a first energy range between about zero and about 100 keV and the second signal having a second photon energy in a second energy range between about 100 keV and about 325 keV, and the third signal having a third photon energy in a third energy range between about 325 keV and about 24 Mev, the second energy range being different than the first and third energy range;

measuring an amplitude of a detection spike corresponding to the first photon energy, the second photon energy, and a third photon energy;

converting, by the device, the first signal into a first image data set, the second signal into a second image data set, and the third signal into a third image data set;

processing, by the device, an image operation on the first, second, and third image data sets to obtain an energy-resolved scatter image data; and distinguishing, by the device in real-time, normal tissue from diseased tissue in the treatment region using the energy-resolved scatter image data.

15. The method of claim 14, comprising:

assigning the first image data set into a first color channel;

assigning the second image data set into a second color channel;

assigning the third image data set into a third color channel; and combining the first image data set in the first color channel, the second image data set in the second color channel, and the third image data set in the third color channel to obtain the energy-resolved scatter image data set with multiple colors.

16. The method of claim 14, comprising:

multiplying the first image data set by a first numerical factor to obtain a fourth image data set;

multiplying the second image data set by a second numerical factor to obtain a fifth image data set; and subtracting the fourth image data set from the fifth image data set to obtain the energy-resolved scatter image data set.

17. The method of claim 14, comprising injecting a contrast agent into the patient.

18. The method of claim 14, comprising injecting iodine into the patient.

* * * * *